(12) United States Patent
Rohling

(10) Patent No.: US 10,660,667 B2
(45) Date of Patent: May 26, 2020

(54) APPARATUS, SYSTEM AND METHOD FOR IMAGING A MEDICAL INSTRUMENT

(71) Applicant: The University of British Columbia, Vancouver (CA)

(72) Inventor: Robert Rohling, Vancouver (CA)

(73) Assignee: The University of British Columbia, Vancouver, British Columbia (CA)

(*) Notice: Subject to any disclaimer, the term of this patent is extended or adjusted under 35 U.S.C. 154(b) by 519 days.

(21) Appl. No.: 14/776,380

(22) PCT Filed: Mar. 13, 2014

(86) PCT No.: PCT/CA2014/000249
§ 371 (c)(1),
(2) Date: Sep. 14, 2015

(87) PCT Pub. No.: WO2014/138918
PCT Pub. Date: Sep. 18, 2014

(65) Prior Publication Data
US 2016/0022308 A1 Jan. 28, 2016

Related U.S. Application Data

(60) Provisional application No. 61/780,189, filed on Mar. 13, 2013.

(51) Int. Cl.
*A61B 17/34* (2006.01)
*A61B 8/08* (2006.01)
(Continued)

(52) U.S. Cl.
CPC ........ *A61B 17/3403* (2013.01); *A61B 8/0841* (2013.01); *A61B 8/14* (2013.01);
(Continued)

(58) Field of Classification Search
CPC ... A61B 17/3403; A61B 8/4411; A61B 8/483; A61B 8/0841; A61B 8/4245;
(Continued)

(56) References Cited

U.S. PATENT DOCUMENTS 4,402,324 A   9/1983 Lindgren et al.
5,758,650 A   6/1998 Miller et al.
(Continued)

OTHER PUBLICATIONS

Brattain, Laura J., et al., "Simple and Effective Ultrasound Needle Guidance System," *33rd Annual International Conference of the IEEE EMBS, Boston*, Massachusetts USA, Aug. 30-Sep. 3, 2011, pp. 1-4.
(Continued)

*Primary Examiner* — Sanjay Cattungal
(74) *Attorney, Agent, or Firm* — Saliwanchik, Lloyd & Eisenschenk

(57) ABSTRACT

Provided is an apparatus, a system and method for use in image guided medical instrument manipulation. Embodiments describe various apparatuses having a mount operable to receive an imaging probe, a body guide and a medical instrument guide. There are also described methods and a systems for using the various apparatuses to position the apparatus and collect data relating to the position of the medical instrument relative to a target within a patient's body. Further methods include using the apparatus and system in epidural anaesthetic procedure or lumbar puncture. The apparatus may include a hand-held ultrasound probe, configured to acquire a volumetric dataset representing a 3-D depiction of a volume, which may include information about a medical instrument's position relative to the target in three dimensions.

27 Claims, 18 Drawing Sheets

(51) Int. Cl.
 A61B 8/14 (2006.01)
 A61B 8/00 (2006.01)
 A61M 5/46 (2006.01)
(52) U.S. Cl.
 CPC .......... *A61B 8/4209* (2013.01); *A61B 8/4245* (2013.01); *A61B 8/4411* (2013.01); *A61B 8/483* (2013.01); *A61B 17/3401* (2013.01); *A61M 5/46* (2013.01); *A61B 8/4444* (2013.01); *A61B 2017/3413* (2013.01)
(58) Field of Classification Search
 CPC ..... A61B 8/4209; A61B 8/14; A61B 17/3401; A61B 8/4444; A61B 2017/3413; A61M 5/46
 USPC .................................................. 600/437–469
 See application file for complete search history.

(56) References Cited

U.S. PATENT DOCUMENTS

| | | | |
|---|---|---|---|
| 5,928,219 | A | 7/1999 | Friend et al. |
| 6,485,426 | B2 | 11/2002 | Sandhu |
| 7,727,192 | B2 | 6/2010 | Tokumoto et al. |
| 2002/0123689 | A1* | 9/2002 | Furia ................... A61B 8/0833 600/461 |
| 2002/0156376 | A1* | 10/2002 | Wang ................... A61B 8/0833 600/439 |
| 2004/0267121 | A1 | 12/2004 | Sarvazyan et al. |
| 2005/0171430 | A1* | 8/2005 | Zhang ................... A61B 8/0825 600/437 |
| 2006/0106306 | A1* | 5/2006 | Essner ................. A61B 8/0833 600/436 |
| 2006/0129046 | A1 | 6/2006 | Stevens et al. |
| 2007/0167817 | A1* | 7/2007 | Huang ................. A61B 8/0833 600/461 |
| 2009/0005687 | A1 | 1/2009 | Kawae |
| 2009/0149812 | A1 | 6/2009 | MacAulay |
| 2011/0245659 | A1 | 10/2011 | Ma et al. |
| 2011/0301451 | A1* | 12/2011 | Rohling ................... A61B 8/00 600/424 |
| 2012/0289820 | A1* | 11/2012 | Rohling ............... A61B 8/0841 600/424 |
| 2013/0229504 | A1* | 9/2013 | Cheng ................. A61B 8/0833 348/65 |
| 2015/0320391 | A1* | 11/2015 | Yao ....................... A61B 8/462 600/424 |
| 2016/0119529 | A1* | 4/2016 | Stolka ................. A61B 8/0841 348/211.1 |

OTHER PUBLICATIONS

Chin, Ki Jinn, et al., "Needle Visualization in Ultrasound-Guided Regional Anesthesia: Challenges and Solutions," *Regional Anesthesia and Pain Medicine*, Nov.-Dec. 2008, 33(6):532-544.

Malenfant, P-A., et al., "Accuracy of 3D Ultrasound for Identification of Epidural Needle Skin Insertion Point in Parturients: A Prospective Observational Study," Abstract :#S-02 *The Society for Obstetric Anesthesia and Perinatology (SOAP) 46th Annual Meeting 2014*, p. 308 of syllabus, May 14-18, 2014, Toronto, Ontario, Canada.

* cited by examiner

APPARATUS, SYSTEM AND METHOD FOR IMAGING A MEDICAL INSTRUMENT

CROSS-REFERENCE TO RELATED APPLICATIONS

This application is a National Stage Application of International Application No. PCT/CA2014/000249, filed Mar. 13, 2014; which claims the benefit of U.S. Provisional Application Ser. No. 61/780,189, filed Mar. 13, 2013, both of which are incorporated herein by reference in their entirety.

FIELD OF INVENTION

This invention relates generally to medical imaging, and in particular relates to an apparatus, system and method for positioning an imagining probe relative to a medical instrument. The invention may further relate to positioning the probe and medical instrument on a patient's body and may also relate to imaging a medical instrument while being inserted inside the patient's body.

BACKGROUND

Some medical procedures require a needle or needle-like instrument to be inserted into a patient's body to reach a target. Examples of these procedures include tissue biopsies, drug delivery, drainage of fluids, ablation for cancer treatment, and catheterization. Some of these procedures can be done manually without any additional guidance other than the sense of feel and visualization of the surface of the body. Other procedures are difficult to perform without additional guidance because the target is deep, the target is small, sense of feel is inadequate for recognizing when the needle's tip has reached the target, or there is a lack of visual landmarks on the body surface. In those cases, providing the doctor with an image of the interior of the body in the vicinity of the target could be beneficial. It would be particularly beneficial to provide real-time images of both the target and the needle as it progresses towards the target.

A particularly challenging needle insertion procedure is required in epidural anaesthesia, often referred to as an "epidural" in the field of obstetrics. Epidural anaesthesia is administered in the majority (>80% of women in labour) of patients for pain relief of labour and delivery in North American hospitals. Epidural anaesthesia involves the insertion of a needle into the epidural space in the spine. The anatomy of the back and spine, in order of increasing depth from the skin, includes the skin and fat layers, a supraspinous and interspinous ligament, the epidural space, the dura mater and spinal cord. A doctor must insert the needle through these layers in order to reach the epidural space without over-inserting the needle and puncturing the thin dura mater surrounding the spinal cord.

The traditional procedure of epidural needle insertion may be as follows. The patient is seated with the doctor facing the patient's back. The doctor chooses a puncture site between the vertebrae based on feeling the protruding spinal processes. After choosing an insertion point on the body, the doctor typically inserts the needle in a plane midline with the long axis of the spine. A saline-filled syringe is attached to the needle so the doctor can apply pressure to the plunger of the syringe, as the needle in incrementally advanced toward the epidural space, and feel how easily saline is injected into the tissue. This is called the "loss-of-resistance" method because resistance falls when the needle tip enters the epidural space. In this way, the sense of feel is the main method for determining when the needle tip has reached the epidural space because the saline is easily injected into the epidural space compared to the tissue encountered before the epidural space. This method can result in failure rates of 6 to 20% depending on the experience and training of the doctor. Complications include inadvertent dura puncture resulting in loss of cerebral spinal fluid and headache, as well as nerve injury, paralysis and even death. Image guidance during needle insertion would improve the accuracy of needle insertion by providing better feedback to the doctor of where the needle is located with respect to the anatomical structures including the target.

In the past several years, ultrasound has been explored as a means to provide a pre-puncture estimate of the depth of the epidural space to correctly place the needle tip. This entails an ultrasound scan prior to needle insertion so that the doctor uses the knowledge of how deep to expect the epidural space when inserting the needle. This use of pre-puncture ultrasound at the planning stage for epidural guidance has received wide interest from the anaesthesia community. It is called pre-puncture ultrasound scanning because the ultrasound is used before, but not during, needle insertion. The National Institute for Health and Clinical Excellence (NICE) has recently issued full guidance to the NHS in England, Wales, Scotland and Northern Ireland on ultrasound-guided catheterization of the epidural space (January 2008). While pre-puncture scanning is a useful advance, doctors still face challenges associated with performing needle insertion procedures without information provided by real-time imaging.

Another similar needle insertion procedure is a lumbar puncture, where a needle is inserted through both the ligamentum flavum and the dura mater into the subarachnoid space to collect cerebrospinal fluid (CSF) for diagnostic and sometimes for therapeutic purposes. Failure to penetrate the subarachnoid space with the spinal needle may require the need for fluoroscopy-guided lumbar puncture to achieve correct localization of the needle.

There have been a small number of published reports describing real-time ultrasound imaging for needle insertion procedures. However, none of these approaches have proven to be entirely satisfactory. Problems include overly limiting views of the images of the target and needle due to poor reflection of ultrasound waves, and/or inherent limitations in the ultrasound equipment. Holding an ultrasound probe in one hand, and advancing a needle into the body with the other hand leaves no hands free to attach a syringe to the needle and press the plunger to detect a loss of resistance. A conventional needle guide can be attached to the ultrasound probe to hold the needle in place, but needle guides with closed channels do not allow for easy removal of the needle from the needle guide when the tip has reached the sensitive target in the spine. Conventional needle guides mounted to an ultrasound probe are typically used with the probe pointing directly to the target (i.e. with the probe face perpendicular to the body surface) and the needle inserted at a non-perpendicular angle to the body surface. Such operation of conventional needle guides is typical for standard 2D ultrasound probes because the needle must fall within the 2D imaging plane yet the probe is directly above the target; the needle must puncture the body surface to the side of the probe and proceed toward the target at an angle of approximately 20 to 60 degrees to the body surface.

SUMMARY

For many needle insertion procedures, such as epidurals and lumbar punctures, it is preferred that the needle insertion be perpendicular to the body surface to provide the shortest path through the body to the target. The present disclosure provides for some solutions to at least some of the deficiencies in the prior art.

In accordance with a first aspect, there is provided an apparatus, the apparatus including: a mount operable to receive an ultrasound probe; a body guide positionable relative to the mount such that the ultrasound probe is positioned to be in contact with a body at an ultrasound probe angle from which a propagation axis extends toward a target in a body and intersects the target; and a medical instrument guide operable to receive and guide a medical instrument substantially perpendicular relative to the plane of the body guide; wherein the ultrasound probe, positioned within the mount, is operable to acquire a volumetric dataset representing a 3-D depiction of a volume such that the volumetric dataset comprises information about the medical instrument's position relative to the target in three dimensions.

In accordance with another aspect, there is provided an apparatus, the apparatus including: a body guide having a planar surface operable to position the apparatus adjacent a body; a medical instrument guide operable to receive and guide a medical instrument substantially perpendicular relative to the plane of the body guide; and a mount positioned adjacent the body guide and the medical instrument guide, wherein the mount is operable to receive an ultrasound probe; wherein the ultrasound probe, positioned within the mount, is operable to acquire a volumetric dataset representing a 3-D depiction of a volume such that the volumetric dataset comprises information about the medical instrument's position relative to the target in three dimensions within the body. The mount may be operable to hold the ultrasound probe in contact with the body at an ultrasound probe angle whereby a propagation axis extends toward the target in the body.

The apparatus may further include the ultrasound probe.

In accordance with another aspect, there is provided an apparatus, the apparatus including: an ultrasound probe, configured to acquire a volumetric dataset representing a 3-D depiction of a volume; a body guide positionable relative to the ultrasound probe such that the ultrasound probe is positioned to be in contact with a body at an ultrasound probe angle from which a propagation axis extends toward a target in a body and intersects the target; and a medical instrument guide operable to receive and guide a medical instrument substantially perpendicular relative to the plane of the body guide; wherein the volumetric dataset comprises information about the medical instrument's position relative to the target in three dimensions.

The ultrasound probe may be configured to acquire a volumetric dataset representing a 3-D depiction of a volume. The probe may be a mechanical 3-D probe or a multidimensional probe. The probe may be curved. In this way, a wide field of view of the anatomy can be obtained with a relatively small footprint of the probe. Moreover, the probe can be angled towards the propagation axis. Accordingly, the beams may intersect the needle or other medical instrument.

The ultrasound probe angle may be between 10 degrees and 80 degrees. The ultrasound probe angle may be anywhere between 5° and 85°. Alternatively, the ultrasound probe angle may be between 10° and 80°. The ultrasound probe angle may be selected from one of the following ranges: 5° and 85°; 10° and 80°; 15° and 75°; 20° and 70°; 25° and 65°; 30° and 60°; 35° and 55°; and 40° and 50°. Alternatively, the ultrasound probe angle may be selected from one of the following: 5°; 6°, 7°; 8°; 9°; 10°; 11°; 12°; 13°; 14°; 15°; 16°, 17°; 18°; 19°; 20°; 21°; 22°; 23°; 24°; 25°; 26°, 27°; 28°; 29°; 30°; 31°; 32°; 33°; 34°; 35°; 36°; 37°; 38°; 39°; 40°; 41°; 42°; 43°; 44°; 45°; 46°, 47°; 48°; 49°; 50°; 51°; 52°; 53°; 54°; 55°; 56°; 57°; 58°; 59°; 60°; 61°; 62°; 63°; 64°; 65°; 66°, 67°; 68°; 69°; 70°; 71°; 72°; 73°; 74°; 75°; 76°, 77°; 78°; 79°; 80°; 81°; 82°; 83°; 84°; and 85°.

The body guide may be operable to be in contact with a locally flat portion of the body. The propagation axis of the medical instrument guide may be substantially perpendicular to the flat portion of the body.

The medical instrument guide may be an open channel. The medical instrument guide may be a closed channel. The medical instrument guide may be an open channel, having a finger pad on either side of the channel. The medical instrument guide may be detachably mountable to the mount in one or more orientations. The medical instrument guide may have a reference mark to assist in determining the depth of the medical instrument insertion along the propagation axis. The medical instrument guide may include a means for tracking the position of the instrument relative to the probe. The ultrasound probe may be configured to acquire the volumetric dataset continuously so that the volumetric dataset includes real-time or semi-real-time information about the position of the medical instrument relative to the target in three dimensions. The ultrasound probe may be configured to acquire the volumetric dataset for the smallest volume that encloses the medical instrument and the target. The mount may include markings representing the inferior-superior and left-right axes of the body thereby indicating the desired position of the apparatus on the body. The mount may be a housing having a geometric shape that substantially matches the geometric shape of a portion of the probe thereby providing a preferred position of the mount on the probe. The mount may have a housing having one or more markings that align with markings on the probe thereby indicating a preferred position of the mount on the probe. The mount may have a housing made from a single piece of flexible material that houses the probe and the medical instrument guide is a channel extending through the housing. The mount may have a housing that houses the probe and the medical instrument guide is an open channel in the form of a groove across the housing. The mount may have a housing that houses the probe and the medical instrument guide is an open channel in the form of a groove across an approximately flat section of the housing that provides a stable landing for the finger securing the instrument in the channel. The mount may have a housing that houses the probe and the medical instrument guide comprises an open channel in the form of a groove across an approximately flat section of the housing and the medical instrument guide further comprises two or more v-shaped notches adjacent to the channel to provide a controlled pathway for the instrument to be inserted into the channel. The medical instrument guide may be positioned at least one centimeter above the surface of the body leaving a gap for grasping of the instrument.

The apparatus may further include a grommet that can be attached to the medical instrument at a location relative to the reference mark thereby indicating a desired depth of the medical instrument insertion.

The mount may also have markings representing the inferior-superior and left-right axes of the body thereby indicating the desired position of the apparatus on the body. In this way, the operator can easily determine the orientation and position the apparatus onto the body.

In accordance with another aspect, there is provided a system for acquiring and displaying ultrasound medical images, including: (a) an ultrasound imaging and instrument guiding apparatus which includes: a hand-held ultrasound probe, configured to acquire a volumetric dataset representing a 3-D depiction of a volume; a mount to which the probe is mounted; a medical instrument guide positionable relative to the ultrasound probe and configured to receive and guide a medical instrument along a propagation axis to a target in a body such that the target and the propagation axis intersect in the volume; and a body guide positionable relative to the ultrasound probe and configured to be in contact with the body at an orientation from which the propagation axis can be referenced; (b) circuitry communicative with the ultrasound imaging and instrument guiding apparatus to receive the volumetric dataset therefrom and comprising a processor with a memory having programmed thereon steps and instructions for execution by the processor to: condition the volumetric datasets; calculate an image plane that coincides with the propagation axis; create a thick-slice image, wherein the thick-slice image represents data from a slab of non zero thickness of the volume encompassing the calculated image plane; and (c) a display device communicative with the circuitry to receive and display one or more of the thick-slice images.

In accordance with another aspect, there is provided a system for acquiring and displaying ultrasound medical images, including: (a) an ultrasound imaging and instrument guiding apparatus which includes: an ultrasound probe, configured to acquire a volumetric dataset representing a 3-D depiction of a volume such that the volumetric dataset comprises information about the medical instrument's position relative to the target in three dimensions; a body guide positionable relative to the ultrasound probe such that the ultrasound probe is positioned to be in contact with a body at an ultrasound probe angle from which a propagation axis extends toward a target in a body and intersects the target; and a medical instrument guide operable to receive and guide a medical instrument substantially perpendicular relative to the plane of the body guide; (b) circuitry communicative with the ultrasound imaging and instrument guiding apparatus to receive the volumetric dataset therefrom and comprising a processor with a memory having programmed thereon steps and instructions for execution by the processor to: condition the volumetric datasets; calculate an image plane that coincides with the propagation axis; create a thick-slice image, wherein the thick-slice image represents data from a slab of non zero thickness of the volume encompassing the calculated image plane; and (c) a display device communicative with the circuitry to receive and display one or more of the thick-slice images.

The memory may be further programmed to enhance the thick-slice image. The memory may be further programmed to superimpose a graphical overlay representing the propagation axis of the instrument on the image. The medical instrument guide may have a reference mark to assist in determining the depth of the medical instrument insertion along the propagation axis, wherein the memory is further programmed to superimpose a graphical overlay representing an anticipated trajectory along the propagation axis of the medical instrument including graduations indicating the depth of the medical instrument insertion with respect to the reference mark on the medical instrument guide. The system may further include a storage device to record the thick-slice image. The thick slice of the volume may be oriented in the sagittal plane of the body. The thick slice of the volume may be oriented in the transverse plane of the body. The image may be created from the thick slice of the volume by a process of merging data in a direction perpendicular to the cross-sectional plane of the thick slice. The size of the volume acquired by the probe may be determined so that it minimally encompasses the maximum extents of the thick slice used to create the image. The reference mark of the medical instrument guide may be referenced to show the depth of the thick slice of the volume along the propagation axis.

The position of the propagation axis relative to the volumetric dataset may be predetermined by measurement of the position of the medical instrument guide relative to the mount. This predetermined measurement can be described as a calibration.

The memory may be further programmed to enhance the thick-slice image. Moreover, the memory can be further programmed to superimpose a graphical overlay representing the propagation axis of the instrument on the image.

The medical instrument guide may have a reference mark from which the depth of the medical instrument insertion along the propagation axis may be referenced and the memory can be further programmed to superimpose a graphical overlay representing an anticipated trajectory of the medical instrument along the propagation axis, including graduations indicating the depth of the medical instrument insertion with respect to the reference mark on the medical instrument guide.

The thick slice image may be created from the thick slice of the volume by a process of merging data in a direction perpendicular to the cross-sectional plane of the thick slice. The size of the volume acquired by the probe may be determined in a manner that it minimally encompasses the maximum extents of the thick slice used to create the image. In this way, the probe may acquire the smaller volume faster and the smaller volume can be processed by the circuit faster.

The reference mark of the medical instrument guide may be referenced to show the depth of the thick slice of the volume along the propagation axis. In this way, the reference mark readings on the medical instrument guide and the displayed depth may work in collaboration.

In accordance with another aspect, there is provided a method of using the apparatus described herein in an epidural anaesthetic procedure, including: placing the apparatus over a back of a patient such that the medical instrument guide is placed over a needle insertion point on the back, and emitting an ultrasound signal into the back and acquiring a volumetric dataset representing a 3-D depiction of a volume, wherein the volumetric dataset includes a section of the patient's spine.

In accordance with another aspect, there is provided a method of using the apparatus described herein in a lumbar puncture procedure, including: placing the apparatus over a back of a patient such that the medical instrument guide is placed over a needle insertion point on the back, and emitting an ultrasound signal into the back and acquiring a volumetric dataset representing a 3-D depiction of a volume, wherein the volumetric dataset includes a section of the patient's spine.

The target may be an epidural space. The target may be a subarachnoid space. The probe may be placed at a paramedian location with respect to the spine. The probe may be placed over spinae erector muscles of the patient. The image plane may be approximately in the mid-sagittal plane of the spine or may be approximately perpendicular to the long axis of the spine. In this way, the muscle tissue may serve as a "window" that transmits ultrasound particularly well. The method described herein may further include inserting a needle through the medical instrument guide and along the propagation axis that intersects the target, such that the captured images include an image of the needle. The position of the propagation axis relative to the volumetric dataset is predetermined by measurement of the position of the medical instrument guide relative to the mount. The method described herein, wherein a single operator may hold the apparatus with one hand and uses the other hand to insert a needle through the medical instrument guide. The method described herein may further include performing a loss-of-resistance procedure to confirm entry of the needle tip into the epidural space. The method described herein may further include performing a loss-of-resistance procedure to confirm entry of the needle tip into the subarachnoid space. The method described herein may further include removing the needle from the medical instrument guide and performing a loss-of-resistance procedure to confirm entry of the needle tip into the epidural space. The method described herein may further include placing the apparatus paramedian to the sacrum and sliding the apparatus in the caudal-cranial direction while counting the vertebrae displayed on the image and stopping at the location where the medical instrument guide is placed over the needle insertion point on the back. The method described herein may further include placing the apparatus paramedian to the twelfth vertebrae and sliding the apparatus in the cranial-caudal direction while counting the vertebrae displayed on the image and stopping at the location where the medical instrument guide is placed over the needle insertion point on the back. The probe may be placed along the midline centre of the spine and the image of the volume is created from a thick slice of the volume approximately perpendicular to the long axis of the spine. The medical instrument guide may have a reference mark from which the depth of the medical instrument insertion along the propagation axis can be referenced and the memory is further programmed to superimpose a graphical overlay representing an anticipated trajectory of the medical instrument including graduations indicating the depth of the medical instrument insertion with respect to the reference mark on the medical instrument guide; wherein the method may further include: observing the depth of the target according to the graduations on the graphic overlay with respect to the reference mark on the medical instrument guide; inserting the medical instrument through the medical instrument guide, wherein the medical instrument has a plurality of equally spaced etchings; and stopping the medical instrument insertion when the depth of the medical instrument insertion, as indicated by the number of the etchings that passed the reference mark, equals the depth of the target. The medical instrument guide may have a reference mark from which the depth of the medical instrument insertion along the propagation axis can be referenced and the memory is further programmed to superimpose a graphical overlay representing an anticipated trajectory of the medical instrument including graduations indicating the depth of the medical instrument insertion with respect to the reference mark on the medical instrument guide; said method may further include: observing the depth of the target according to the graduations on the graphic overlay with respect to the reference mark on the medical instrument guide; attaching a grommet to the medical instrument at a distance from the inserted tip of the instrument that is equal to the depth of the target with respect to the visible mark on the medical instrument guide; inserting the medical instrument through the medical instrument guide; and stopping the medical instrument insertion when the depth of the medical instrument insertion, as indicated by the distance from the grommet to the reference mark on the medical instrument guide, equals the depth of the target.

The position of the propagation axis relative to the volumetric dataset may be predetermined by measurement of the position of the medical instrument guide relative to the mount. This predetermined measurement can be described as a calibration.

The medical instrument guide may have a reference mark from which the depth of the medical instrument insertion along the propagation axis can be referenced and the memory may be further programmed to superimpose a graphical overlay representing an anticipated trajectory of the medical instrument including graduations indicating the depth of the medical instrument insertion with respect to the reference mark on the medical instrument guide. The method may further comprise: observing the depth of the target according to the graduations on the graphic overlay with respect to the reference mark on the medical instrument guide; inserting the medical instrument through the medical instrument guide, wherein the medical instrument has a plurality of equally spaced etchings; and stopping the medical instrument insertion when the depth of the medical instrument insertion, as indicated by the number of the etchings that passed the reference mark, equals the depth of the target. Alternatively the method may also comprise: observing the depth of the target according to the graduations on the graphic overlay with respect to the reference mark on the medical instrument guide; attaching the grommet to the medical instrument at a distance from the inserted tip of the instrument that is equal to the depth of the target with respect to the reference mark on the medical instrument guide; inserting the medical instrument through the medical instrument guide; and stopping the medical instrument insertion when the depth of the medical instrument insertion, as indicated by the distance from the grommet to the reference mark on the medical instrument guide, equals the depth of the target.

The method may further comprise advancing a medical instrument through the channel while controlling the level of friction between the medical instrument and the channel with the level of force of a finger on the exposed portion of the medical instrument.

According to another aspect, there is provided a method of using the above referenced system, i.e. the system, which includes an ultrasound imaging and instrument guiding apparatus and circuitry communicative with the ultrasound imaging and instrument guiding apparatus. This method comprises: placing the apparatus over a back of a patient such that the medical instrument guide is placed over a needle insertion point on the back, and the body guide is pressed against the body surface to align the medical instrument guide and probe to the body. The method further comprises emitting an ultrasound signal into the back and acquiring a volumetric dataset representing a 3-D depiction of a volume, wherein the dataset includes a section of the patient's spine. The method further comprises conditioning the volumetric datasets, calculating an image plan that coincides with the propagation axis, and creating a thick-slice image, wherein the thick-slice image represents data from a slab of non zero thickness of the volume encompassing the calculated image plane, and displaying one or more of the thick-slice images.

This method can further comprise superimposing a graphical overlay representing the propagation axis of the instrument on the image. The method can also further comprise recording the thick slice image onto a storage device. Further, the method can comprise creating the image from the thick slice of the volume by a process of merging data in a direction perpendicular to the cross-sectional plane of the thick slice.

This method can further comprise holding a needle in the medical instrument guide with the same hand that is holding the apparatus, and advancing the needle into the body with the free hand.

There are also provided uses for the apparatuses and systems described herein. The use may be in epidural or lumbar puncture procedures. The use may be for inserting a medical instrument into a body. There are also provided kits and commercial packages containing the apparatus described. The kits and commercial packages may further comprise instructions for use.

DETAILED DESCRIPTION

Figure 1:
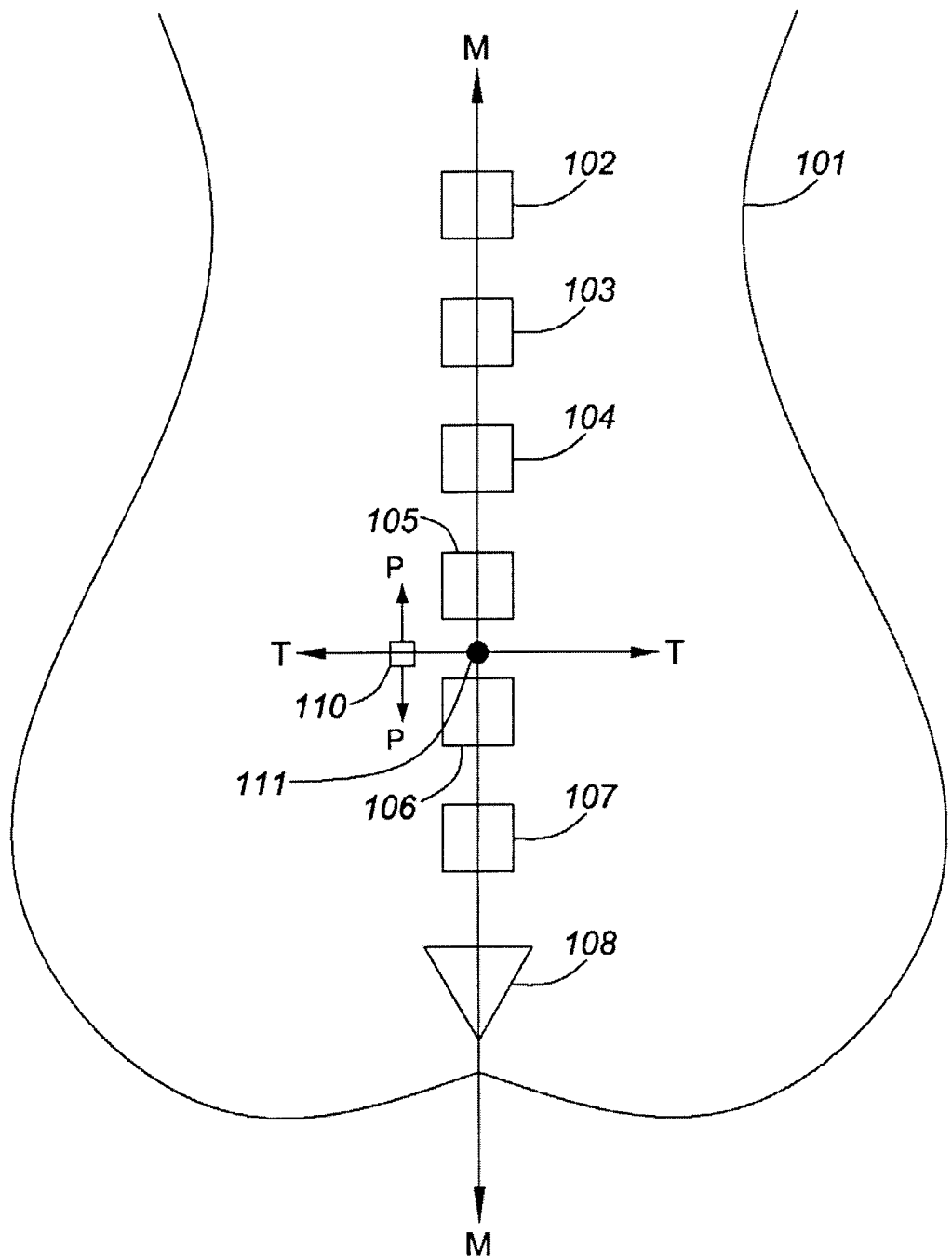
FIG. 1 is a schematic view of approximate locations of vertebrae, needle puncture point, and various imaging planes of a patient to be imaged by an ultrasound probe and subjected to an epidural anaesthesia procedure.

In the following description, the term "operator" as used herein is used to describe the person performing the medical procedure, and is usually a medical doctor specializing in anesthesia, radiology, neurosurgery or neurology, but the term can apply to other medical personnel.

The term "needle" as used herein is an example of a medical instrument that may be inserted into the body, for the sake of illustration. Alternative medical instruments, which may be used with the various embodiments described herein may include an ablation probe, a catheter, a guide wire or another medical instrument that may be inserted into a body and guided by the apparatus towards a target within a patient's body.

The term "ultrasound probe angle" as used herein is meant to be the angle between the between the plane of the body guide and the longitudinal axis of the ultrasound probe. For example, ultrasound probe angle is shown as 802 in FIG. 8A. The ultrasound probe angle may be anywhere between 5° and 85°. Alternatively, the ultrasound probe angle may be between 10° and 80°. The ultrasound probe angle may be selected from one of the following ranges: 5° and 85°; 10° and 80°; 15° and 75°; 20° and 70°; 25° and 65°; 30° and 60°; 35° and 55°; and 40° and 50°. Alternatively, the ultrasound probe angle may be selected from one of the following: 5°; 6°; 7°; 8°; 9°; 10°; 11°; 12°; 13°; 14°; 15°; 16°, 17°; 18°; 19°; 20°; 21°; 22°; 23°; 24°; 25°; 26°, 27°; 28°; 29°; 30°; 31°, 32°; 33°; 34°; 35°; 36°, 37°; 38°; 39°; 40°; 41°; 42°; 43°; 44°; 45°; 46°; 47°; 48°; 49°; 50°; 51°; 52°; 53°; 54°; 55°; 56°, 57°; 58°; 59°; 60°; 61°; 62°; 63°; 64°; 65°; 66°, 67°; 68°; 69°; 70°; 71°; 72°; 73°; 74°; 75°; 76°; 77°; 78°; 79°; 80°; 81°; 82°; 83°; 84°; and 85°.

In the FIGURES the following annotations and numbering are used:

M-M midline; T-T transverse plane;

C-C horizontal axis extending perpendicularly through the body surface at medical instrument insertion point 111;
A-A axis of the apparatus is aligned to M-M;
B-B axis of the apparatus is aligned to T-T;
204 is aligned with C-C;
101 body; 102 T12; 103 L1; 104 L2; 105 L3; 106 L4; 107 L5; 108 sacrum;
110 position (directly above spinae erector muscle);
111 medical instrument puncture site;
199 mount; 1199 mount; 1999 mount; 299 upper mount and 399 lower mount (two part);
200 medical instrument guiding apparatus, or "apparatus";
2003 medical instrument guiding apparatus, or "apparatus";
202 3-D ultrasound probe or "probe";
2202 3-D ultrasound probe or "probe";
203 medical instrument guide;
1203 medical instrument guide;
2203 medical instrument guide;
204 propagation axis (is aligned to axis C-C of the body);
301 finger;
402 volumetric dataset;
403 thick-slice;
404 target;
405 needle (an example of a medical instrument);
1405 needle (an example of a medical instrument);
603 thick-slice sagittal image;
604 thick-slice transverse image;
605 graduations;
801 body guide; 1801 body guide; 2801 body guide;
802 ultrasound probe angle;
804 v-notches;
805 finger landing;
806 alignment marking;
900 data processing and imaging system, or "system";
901 T/R switch;
902 beam transmitter;
903 beam receiver;
904 signal processor;
905 3-D image rendering module;
906 image memory;
907 system controller;
908 user interface;
909 image display device;
910 storage device;
911 needle guide-to-volume calibration;
1000 data processing method;
1001 step to obtain volume dataset;
1002 step for data conditioning;
1003 step to calculate the thick slice portion of the volume;
1007 step for thick-slice cross-sectional image processing;
1008 step for image enhancement;
1201 reference mark;
1202 grommet; and
1302 graphical overlay(s) [showing trajectory of medical instrument guide 203].

Ultrasound imaging is a technique for imaging the interior of the body with high frequency sound waves. A standard ultrasound probe comprises a set of transducer elements emitting sound waves into the body. The sound waves reflect on tissue or bone in the body and the reflected sound (echo) is detected by the same transducer elements. By calculating the time from emission to detection of the sound waves at each transducer and measuring the intensity of the reflected sound wave an ultrasound image can be constructed that shows various anatomical features in the ultrasound probe's field of view.

Ultrasound scanning during a needle insertion procedure enables the observation of both the needle and the target on a real-time ultrasound display. One advantage of such a real-time ultrasound scanning-assisted needle insertion procedure is the ability for the operator to modify the path of needle insertion to correct the trajectory towards the target. Embodiments described herein relate to an ultrasound imaging and needle guiding apparatus for guiding a needle to a target in a patient's body, such as the epidural space of the spine or the subarachnoid space, and for acquiring real-time ultrasound images of the needle and target. Specifically, these described embodiments provide real-time or near real-time images of both the needle and the surrounding tissue and bone of the body using a 3-D ultrasound probe while the needle is being inserted through a medical instrument guide. In some embodiments, there is an ultrasound imaging and needle guiding apparatus with a 3-D ultrasound probe which is placed in a slightly paramedian position, relative to a midline needle insertion position, which enables the ultrasound imaging and needle guiding apparatus to clearly view both the needle and the target, such as an epidural space. In addition, some of the described embodiments include a method for using the ultrasound imaging and needle guiding apparatus and for processing acquired 3-D volumetric datasets from the ultrasound probe for representation on a 2-D display.

Directional terms such as "top", "bottom", "left" and "right" are used in the following description for the purposes of providing relative reference only, and are not intended to suggest any limitations on how any apparatus or components thereof are to be manufactured or positioned during use. A number of embodiments are described below by way of example only.

Figure 4A:
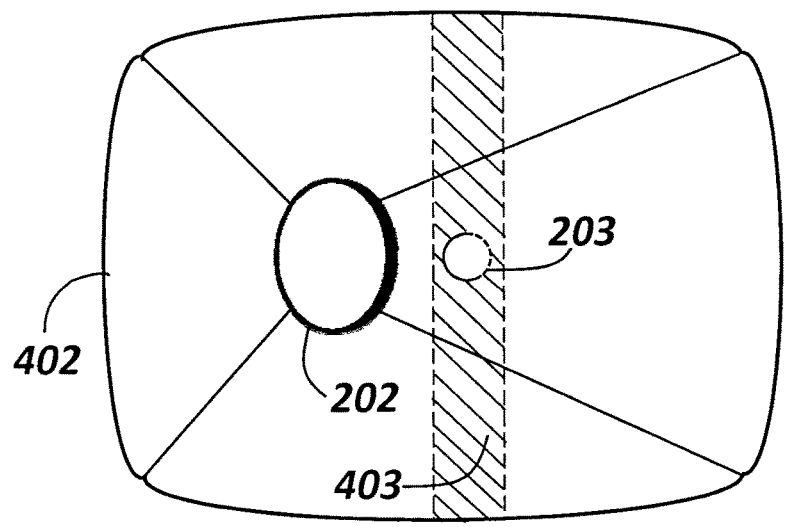
FIG. 4A is a schematic back view of the ultrasound probe and medical instrument guide along with a representation of the thick slice in the sagittal plane of the ultrasound volumetric dataset captured by the ultrasound probe.
Figure 4B:
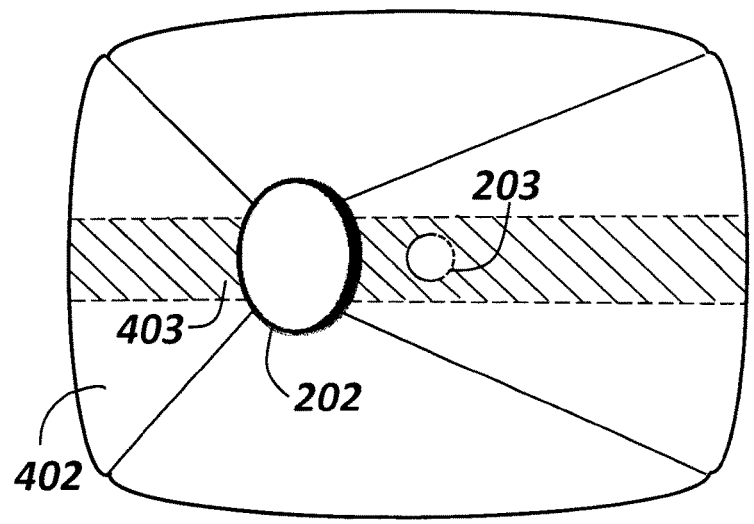
FIG. 4B is a schematic back view of the ultrasound probe and medical instrument guide along with a representation of the thick slice in the transverse plane of the ultrasound volumetric dataset captured by the ultrasound probe.
Figure 5:
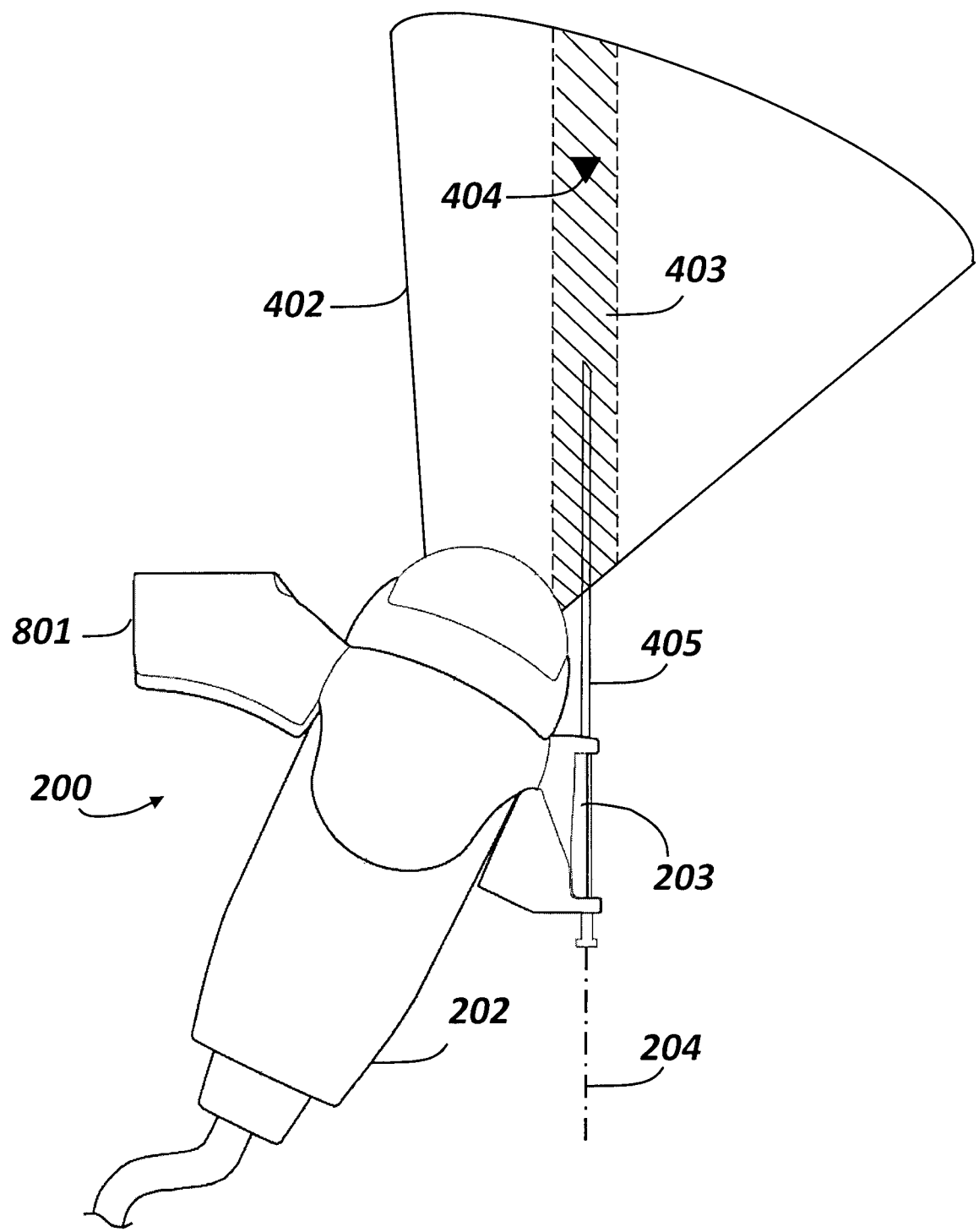
FIG. 5 is a schematic top view of the ultrasound probe of the 3-D ultrasound imaging and needle guiding apparatus along with a representation of the spatial extent of the volumetric dataset captured by the ultrasound probe.
Figure 17:
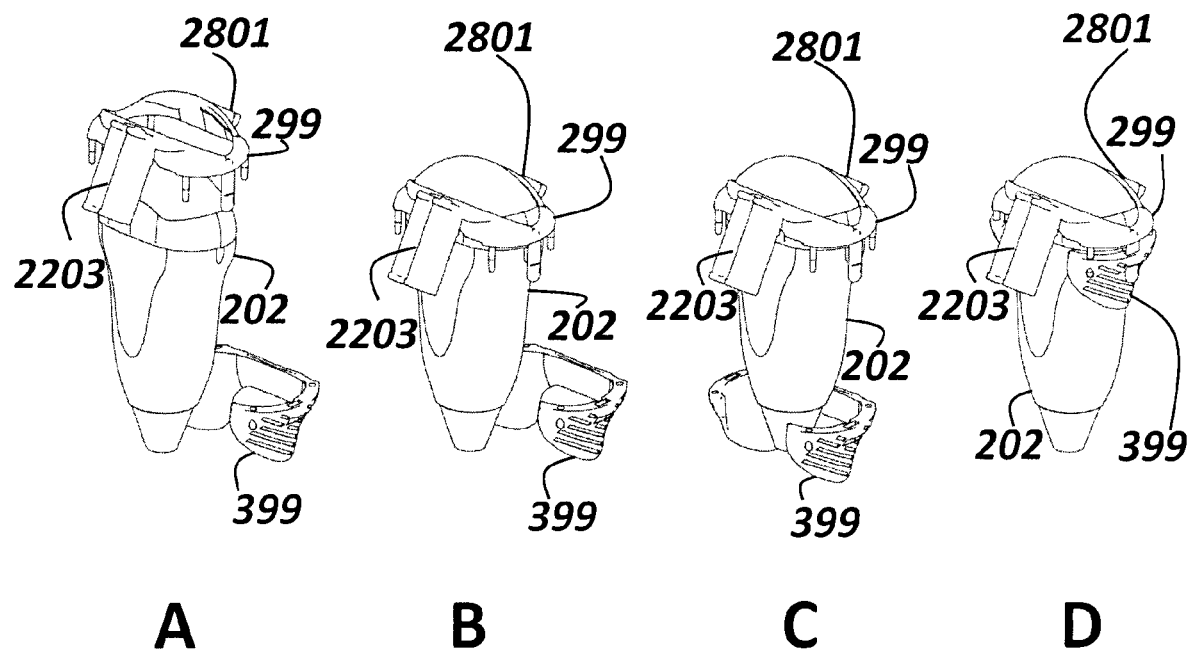
FIG. 17A-D shows an alternative embodiment where the apparatus is in two parts and shows the attachment of the apparatus to a probe.

According to an embodiment and referring to FIGS. 2 to 8, there is provided an ultrasound imaging and needle guiding apparatus 200 that enables the acquisition of simultaneous, or near simultaneous, images of anatomical features within a body, such as a target 404 and a needle 405 (as shown in FIG. 5). Alternatively, the medical instrument may be an ablation probe, a catheter, a guide wire or another medical instrument that may be inserted into a body and guided by the apparatus towards a target within a patient's body. As shown in FIG. 8A, the main components of this embodiment of the apparatus 200 include a 3-D ultrasound probe 202, a mount 199 on the probe 202, a body guide 801 and a medical instrument guide 203 that in this embodiment is affixed to the mount 199 but in other embodiments can be detachably mounted to the mount 199 or remotely located or be attached to or form part of the 3-D ultrasound probe 202. The ultrasound probe 202 is positioned on the mount 199 to provide simultaneous or near-simultaneous 3-D depictions of a volume of interest in the body 101 and of the needle 405, which may be inserted into the volume of interest. The mount 199 in this embodiment is a housing in which probe 202 is housed; alternatively, the mount 199 can be a rectangular mounting plate (not shown) to which the probe 202 is mounted, or a rod or similar-shaped member to which the probe 202 is mounted (not shown). The mount 199 in another embodiment may be a multi-piece housing (FIG. 17 shows a two-piece housing) that is assembled together to house the probe.

Figure 9:
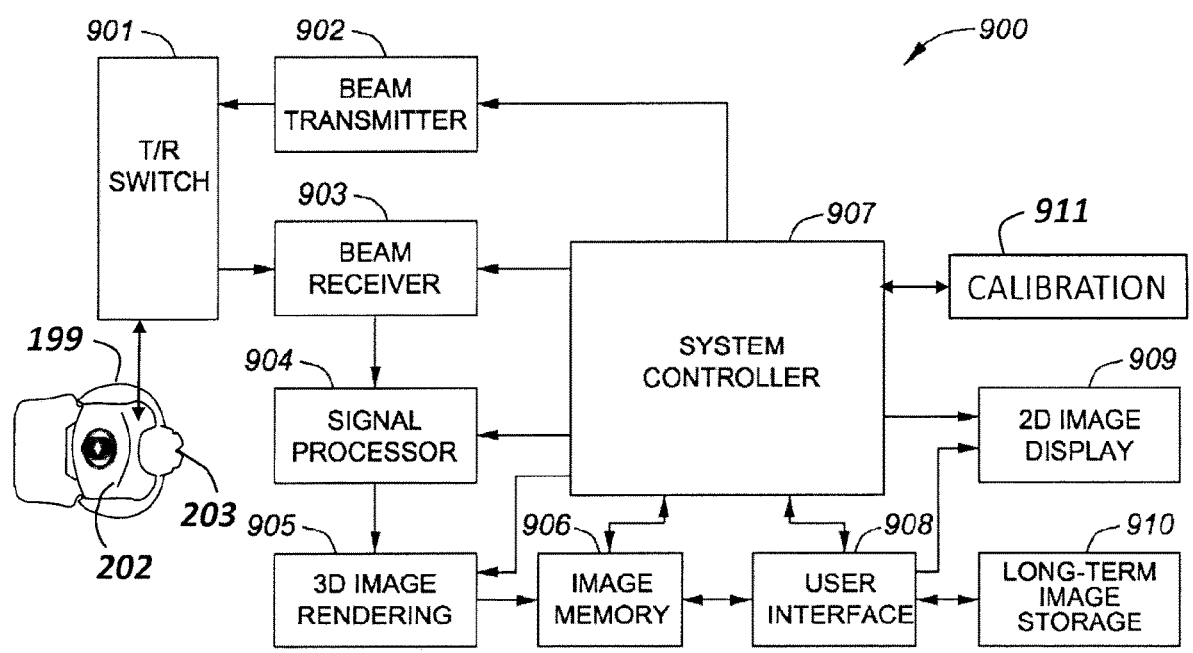
FIG. 9 is a block diagram of an imaging system comprising the 3-D ultrasound imaging and needle guiding apparatus.

As shown in FIG. 9 and as will be described in more detail below, the apparatus may be coupled to a data processing and imaging system 900, which includes circuitry for processing volumetric datasets representing the ultrasound images captured by the probe 202, and an image display device 909 for viewing the processed ultrasound images. As shown in FIGURE ii, the 3-D ultrasound volumetric datasets obtained by the ultrasound probe can be processed and displayed as a single or as multiple image(s) (i.e. 603 and 604) of the volume of interest and the needle 405 inserted into the volume of interest.

One particular application of this apparatus is for imaging the anatomy of a patient's spine and a needle during an epidural injection, in which case the medical instrument is an epidural needle and the target is the epidural space. FIG. 1 shows the lower back of a patient's body 101; the vertebrae of the lower back are the thoracic vertebrae T12 102, lumbar vertebrae L1 103, L2 104, L3 105, L4 106, L5 107 and the sacrum 108. A needle puncture site in shown located between the third lumber vertebra L3 105 and the fourth lumbar vertebrae L4 106 in the midline M-M of the patient's spine and along a transverse T-T plane. The apparatus may be designed as a portable device that an operator can place on the back of the patient undergoing the epidural injection. The apparatus may be positioned near the puncture site 111 such that the operator may image the back and spine underneath the apparatus and detect in the ultrasound image both the major anatomical features of interest and the tip and body of the needle during injection. The probe may be located on the mount such that when the apparatus is placed on the back of the patient with the medical instrument guide directly above the puncture site in, the probe may be located at position 110 directly above the spinae erector muscle; it is expected that the muscle tissue at this location no serves as a "window" that transmits ultrasound particularly well. The probe can also be oriented on the mount such that propagation of the sound waves from the probe is directed towards the spine.

Figure 3:
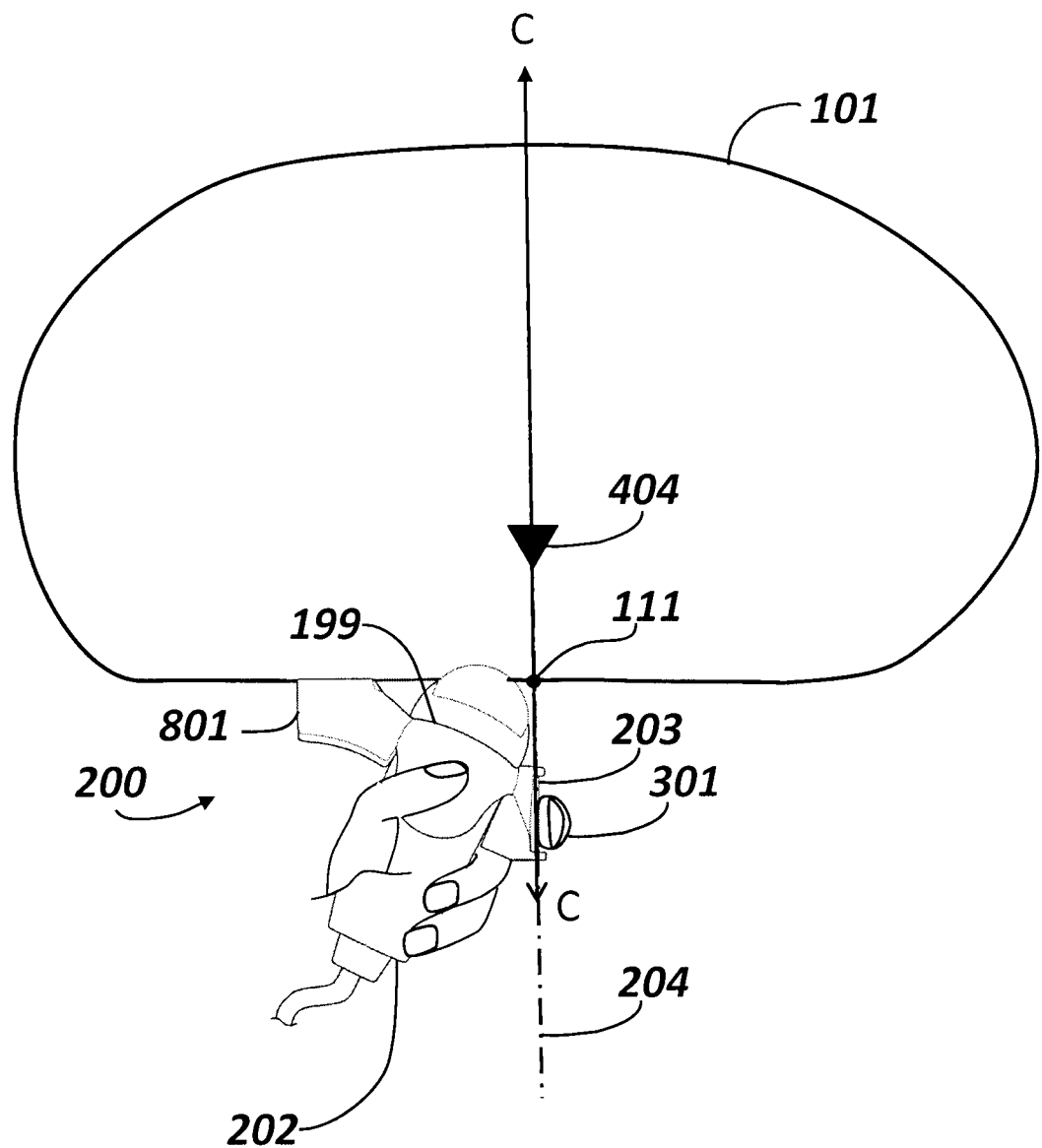
FIG. 3 is a schematic top view of the 3-D ultrasound imaging and needle guiding apparatus and a cross-section of the patient's torso.

As shown in FIG. 3, the back of the mount (i.e. the portion facing away from the body 101 during use) may be shaped and sized to allow for easy single-handed gripping by the operator. The single-handed gripping also allows a finger 301 or thumb of the gripping hand to reach the medical instrument guide 203 and secure a needle or other medical instrument in the guide 203. Although not shown in this FIGURE, the back of the mount 199 can be further provided with finger grips shaped to accept the fingers of the operator. Alternatively, the apparatus may be provided with an easy to grasp handle (not shown) so that the operator may hold the apparatus with one hand comfortably against the patient's back during the procedure.

Figure 6:
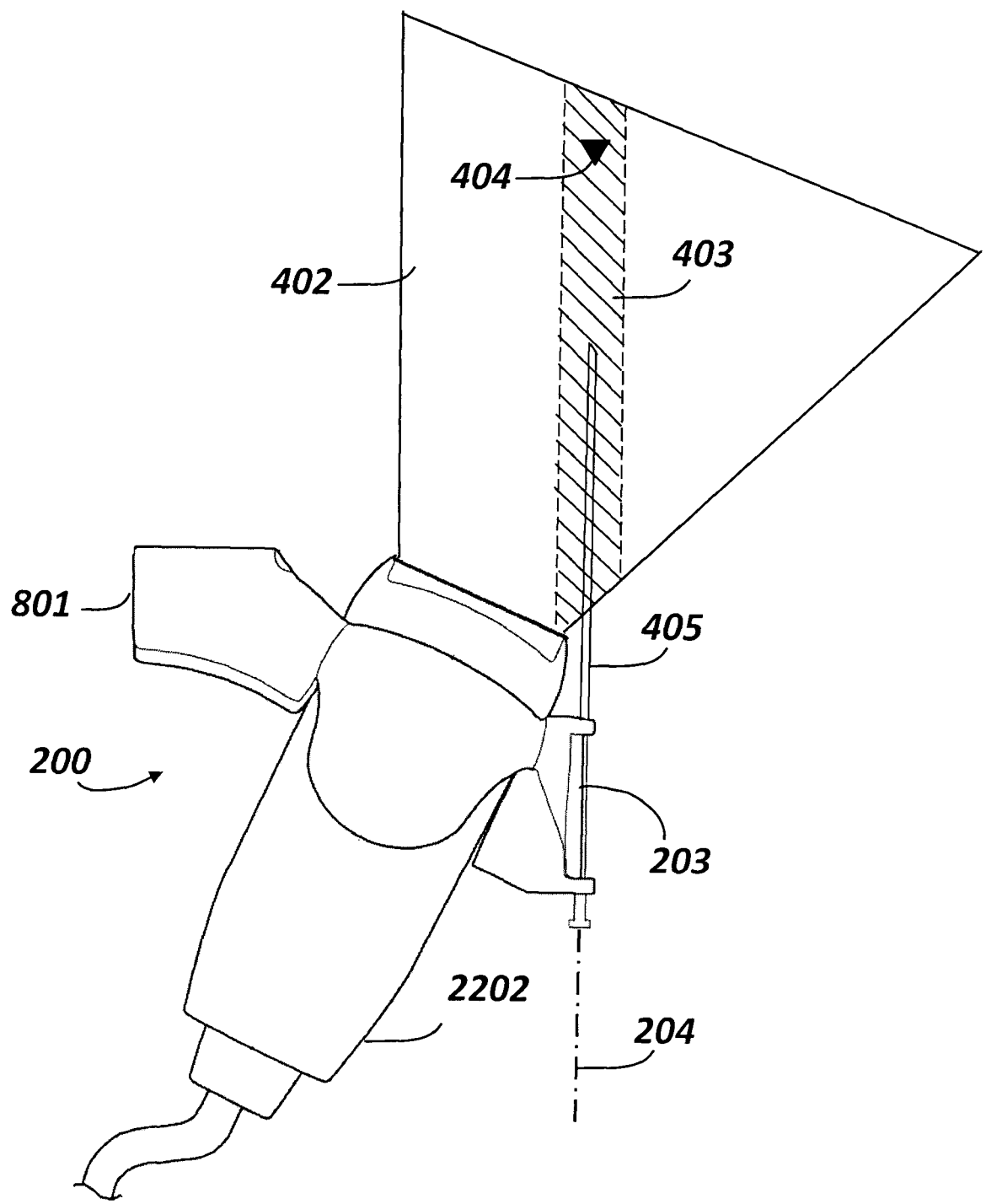
FIG. 6 is a schematic top view of a linear or phased array 3-D ultrasound probe of the imaging and needle guiding apparatus according to another embodiment of the invention, along with a representation of the spatial extent of the volumetric dataset captured by the ultrasound probe.
Figure 7:
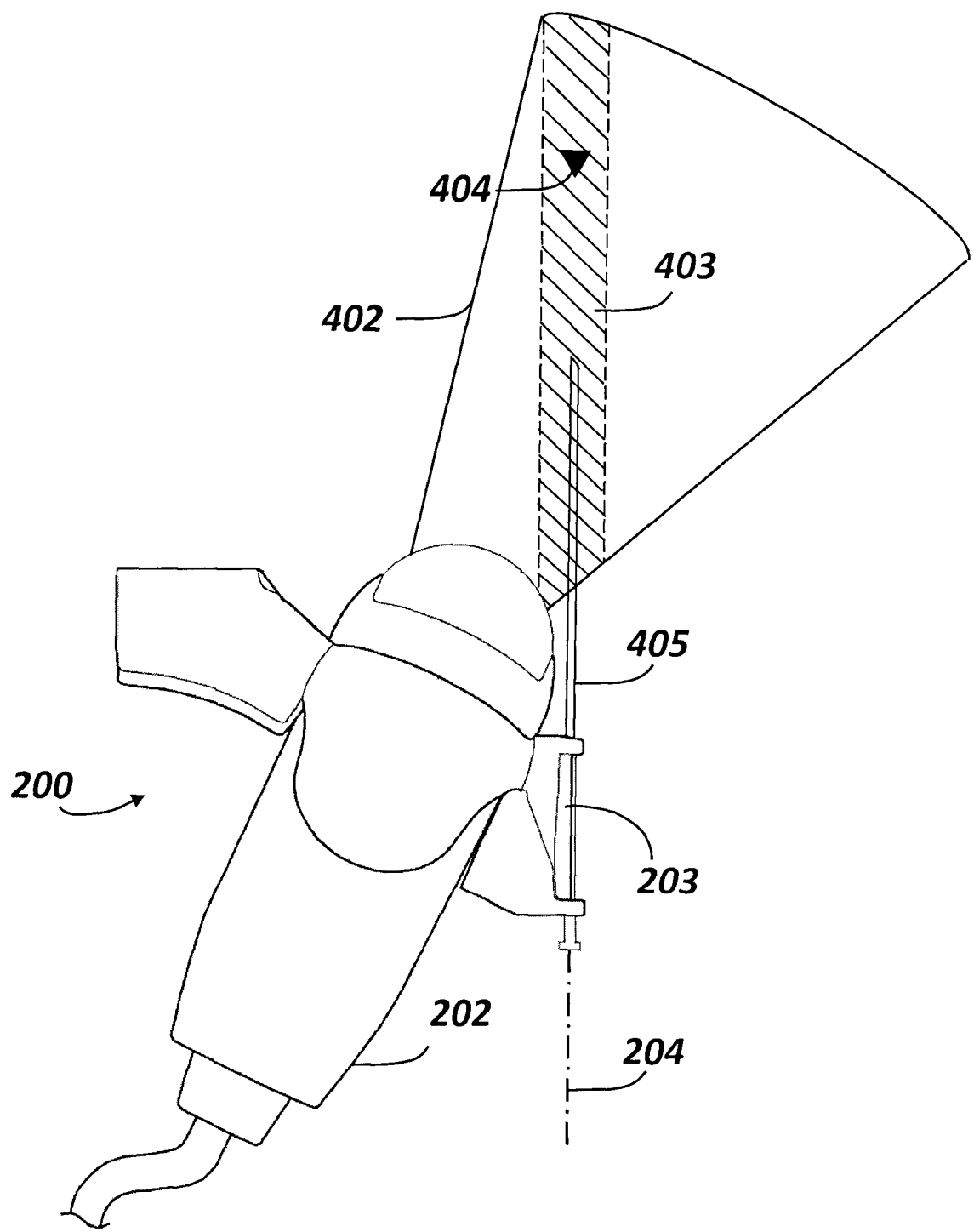
FIG. 7 is a schematic top view of a 3-D ultrasound probe of the imaging and needle guiding apparatus according to another embodiment of the invention, along with a representation of the smallest spatial extent of the volumetric dataset captured by the ultrasound probe that encloses the thick slice.

As shown in FIGS. 5 and 7, the 3-D probe 202 (or similarly the linear or phased array 3-D probe 2202 in FIG. 6) emits sound waves into a 3-D volume that covers the part of the patient's spine underneath the apparatus 200, typically near the L3 and L4 vertebrae. The received data from the reflected sound waves create a volumetric dataset 402 of the anatomy, unlike a 2-D ultrasound probe, which creates images of a cross-sectional plane. The 3-D volumetric dataset 402 may be viewed by the operator in a number of ways. For example, viewing a 2-D image of a thick slice 403 (see FIGS. 4A and 4B) of a slab of the volumetric dataset along a cross-sectional plane of the volume. The 2-D image can be created from the slab of data by merging the data in the direction perpendicular to the cross-sectional plane. The merging involves taking a weighted combination of the data after data conditioning where the weights are chosen to emphasize data representing the medical instrument and target. The ability to view thick slices 403 of the volumetric dataset 402 at a location and angle that matches both the needle propagation axis 204 and the target 404 may be a way to alleviate the limitations of conventional 2-D ultrasound transducers. Furthermore, the ability to view thick slices may be a way to alleviate the limitations of standard cross-sectional imaging where needle bending and uncertainty in the location of the needle propagation axis make it difficult to maintain alignment of the needle in the cross-sectional plane, and thus maintain needle and target visibility in the image.

Real-time 3-D ultrasound imaging can be implemented by at least the following two methods:

1) mechanical sweeping: A specialized 3-D probe is constructed by combining a 2-D probe with a motorized mechanism for rapidly moving the 2-D probe so that the 2-D image sweeps repeatedly through a volume of interest. Repeated sweeping is usually implemented in an oscillating manner where each oscillation produces a 3-D volumetric dataset. The spatial relationship between the set of 2-D images from each oscillation is known because the probe motion is controlled and the images are reconstructed into a 3-D Cartesian volumetric dataset. This device is referred to hereafter as a mechanical 3-D probe;

2) multidimensional arrays: A specialized probe is created without a motorized mechanism, but instead uses a two dimensional array (matrix) of transducers to scan over a 3-D volume of interest. The speed of volume acquisition is typically higher than mechanical probes but the complexity of the probe increases and image quality can be inferior. This probe is known as a multidimensional probe.

The 3-D probe of the apparatus can be a mechanical 3-D probe or a multidimensional 3-D probe as known in the art. An example of a suitable mechanical 3-D probe is the RAB2-5 H46701M for the Voluson 730 ultrasound machine by General Electric Corporation (GE Healthcare™, Chalfont St. Giles, United Kingdom). An example of a suitable multidimensional probe is the X7-2 for the Philips iU22 ultrasound machine (Philips Healthcare™, Andover, Mass., USA). With such types of probes, the rapid creation of 3-D volumetric datasets allows multiple planes of the acquired datasets to be visualized in real-time, thus overcoming some of the limitations of standard 2-D probes. These planes can be selected at any orientation and location within the volume through user control.

Figure 2:
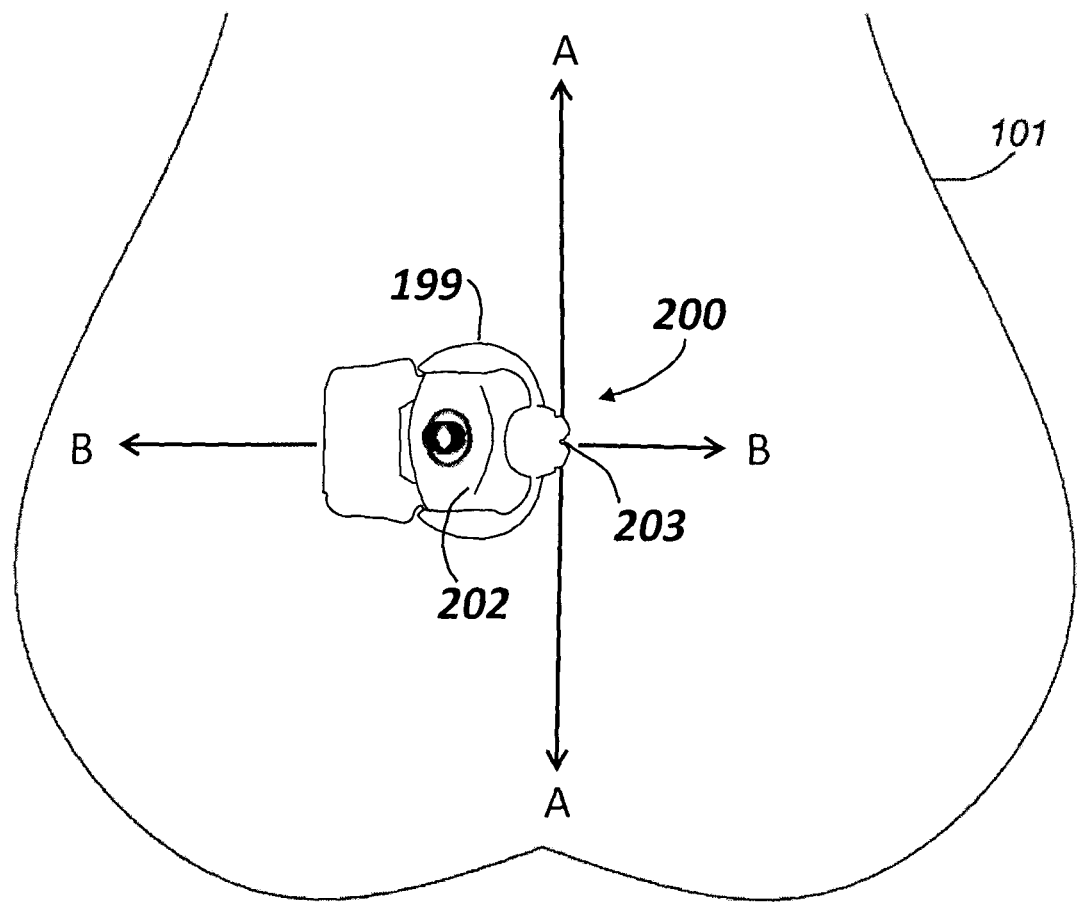
FIG. 2 is a schematic back view of a 3-D ultrasound imaging and needle guiding apparatus according to one embodiment of the invention and positioned to image the spine of the patient shown in FIG. 1.

As shown in FIGS. 3, 5, 6, 7, 8A, 12, 15, the medical instrument guide 203 (or similarly the medical instrument guide 2203 in FIG. 14A, or the medical instrument guide 1203 in FIGS. 16A and 16B) in these embodiments is a channel, which extends through a portion of the mount and is sized to receive the needle 405 (except 14A and 15 needle not shown). The channel can be an open half-cylindrically-shaped channel (groove) to allow easy insertion and removal of the needle from the medical instrument guide. Other embodiments for the medical instrument guide may have holes, slots, apertures, or any guide-way, which serves to constrain the path of the needle during the insertion procedure. The medical instrument guide is positioned beside the 3-D probe and is used to guide the needle along the propagation axis 204 (except 14A and 15 where propagation axis not shown) during the injection procedure. As shown in FIGS. 1, 2 and 3, when the apparatus 200 is placed on the patient's back, the axis A-A of the apparatus 200 is aligned approximately to within 10 to 20 degrees, measured about the axis of the medical instrument guide 203, of the midline axis of the spine M-M (see FIG. 1) in the inferior-superior direction, while the axis B-B of the apparatus 200 is orthogonal to axis A-A and is aligned approximately to extend to the left and right of the patient along transverse axis T-T (see FIG. 1). The propagation axis of the medical instrument guide is aligned approximately with the axis C-C which is the horizontal axis extending perpendicularly through the body surface at the needle insertion point 111 (see FIG. 3) and is directed towards the patient's back in the anterior-posterior direction. The apparatus may be provided with markings (not shown) representing axes A-A, B-B, and the propagation axis to assist the operator in correctly positioning the apparatus against the patient's back during use.

As will be discussed further below, the apparatus obtains volumetric datasets that may be processed by a system described herein (for example, 900 of FIG. 9) and displayed in multiple real-time views, which assist the operator in guiding the medical instrument to the target. Two of these views include the thick slices along the sagittal plane, which is the plane along axes M-M and C-C and the transverse plane, which is the plane along axes T-T and C-C.

Figure 14A:
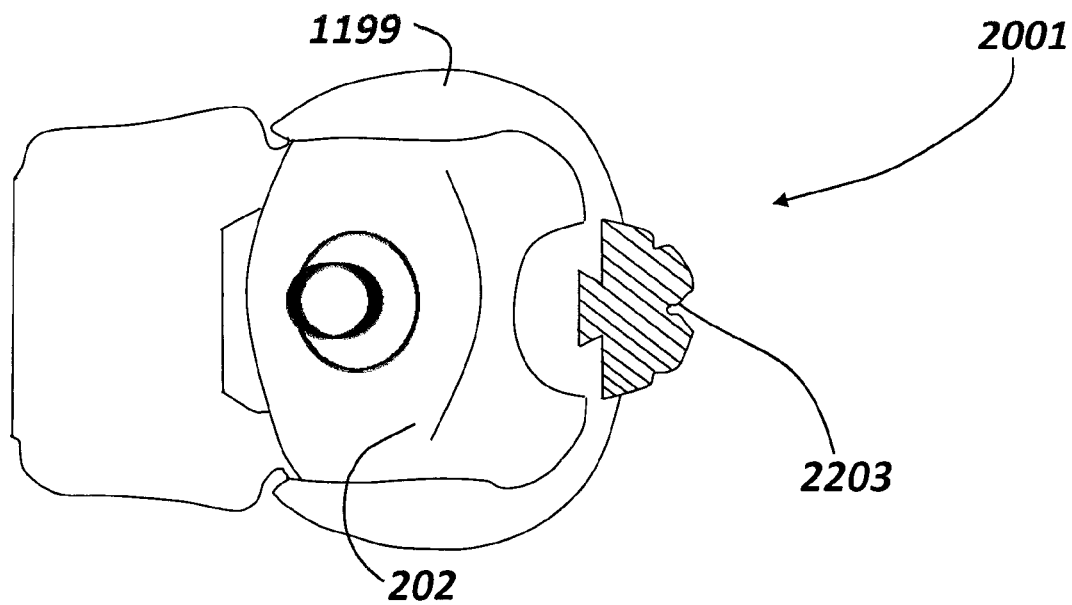
FIG. 14A is a schematic front view of a detachable medical instrument guide with an open channel and FIG. 14B is a schematic front view of the detachable medical instrument guide with a closable channel.
Figure 14B:
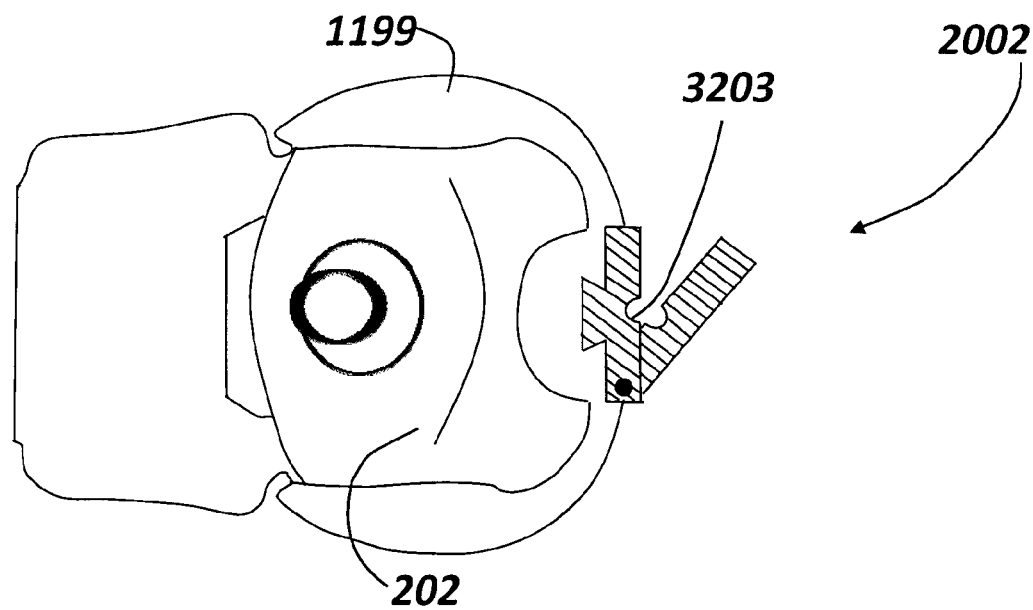

The medical instrument guide 203 may be either be affixed to the apparatus as shown in FIG. 2, 3, 5, 6, 7, 8A, 12, or 15 or the medical instrument guide 2203 may be a separate component which can be detachably mounted to the mount 1199 as shown in FIG. 14A and in FIG. 14B, the medical instrument guide 3203 is a detachable clip having a pivotable member connected about a pivot axis to enclose the channel. In FIGS. 14A and 14B, the apparatus 2001 and 2002, respectively shows a removeable mount 1199 in association with a probe 202. The detachable medical instrument guide can be designed to allow the selection of a particular trajectory to be chosen by mounting one of a series of medical instrument guides, each with a different orientation of the guide-way. The detachable medical instrument guide and the mount may also be disposable after a single use for the purposes of ease-of-sterilization.

As can be seen in FIG. 4, the probe 202 is positioned and operated so that a portion (shown in cross-hatched shading) of the volumetric dataset 402 produced by probe 202 intersects the pathway of the needle inserted through the medical instrument guide 203. FIG. 4A shows a thick slice 403 portion in the sagittal plane. FIG. 4B shows a thick slice 403 portion in the transverse plane. The thickness of the slice is typically 5 mm, but other thicknesses may be used, including a thickness of 0 mm, which is considered a simple cross-sectional image with zero thickness.

As can be seen in FIG. 5, the instrument guide 203 and probe 202 are positioned relative to each other so that the thick slice portion 403 covers a target 404, which represents the epidural space in an embodiment, and the part of the needle pathway leading up the target 404. In FIG. 5, the needle 405 is shown partly inserted into the medical instrument guide 203 in a direction that will intersect the target 404.

Figure 8A:
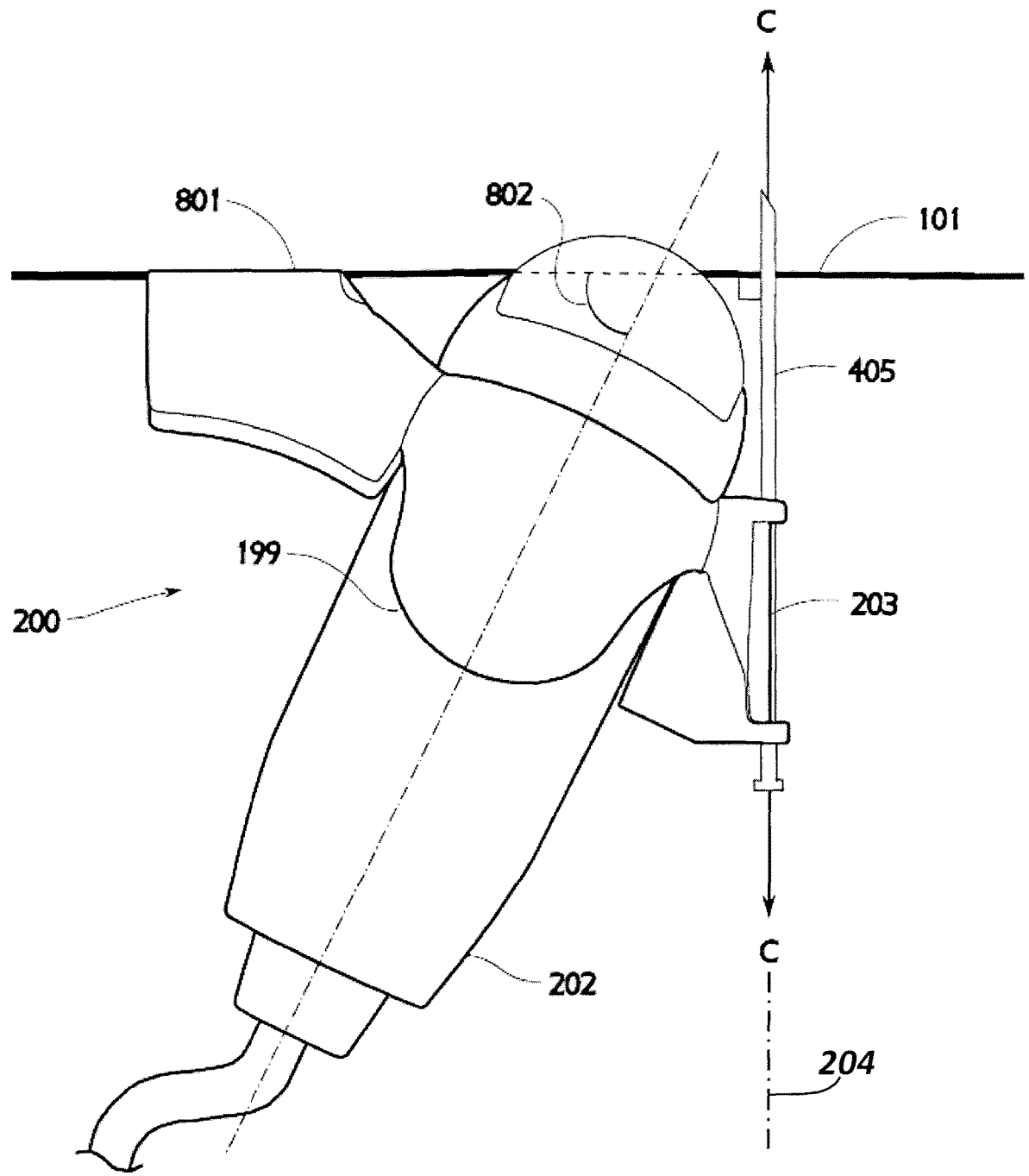
FIG. 8A is a schematic top view of the 3-D ultrasound imaging and needle guiding apparatus and a needle and a representation of the body surface.

Referring to FIG. 8A, the mount 199 contains a body guide 801 that constrains the ultrasound probe 202 and propagation axis 204 of the medical instrument guide 203 to predetermined orientations relative to the body 101. The body guide 801 can be an extension of the mount 199 that lies flat against the body 101. The body guide 801 is pressed against the surface of the body 101 so that the flat portion of the body guide 801 is substantially parallel to the surface of the body 101. This alignment of the body guide 801 with the surface of the body 101 provides an alignment of the propagation axis 204 of the medical instrument guide 203 that is substantially perpendicular to the surface of the body 101 at the preferred needle insertion point. The surface of the body 101 is substantially flat within the region around the needle insertion point that includes the body guide 801. The advantage of the body guide 801 is to ensure that the needle 405 is inserted perpendicular to the surface of the body 101. It should be noted that a substantially perpendicular needle 405 insertion is described here, but in other embodiments may include non-perpendicular angles of the needle insertion into the body depending on the intended use. It should also be noted that the face of the probe can indent the surface of the body 101 slightly to provide good acoustic coupling between the probe and the body without affecting the angle of the body guide 801 or medical instrument guide 203 relative to the body.

The mount 199 can hold the ultrasound probe 202, the medical instrument guide's 203 propagation axis 204 and the body guide 801 at pre-determined angles relative to each other. Moreover, the ultrasound probe angle 802 can lie between the propagation axis 204 of the medical instrument guide 203 and the plane of the body guide 801. For sake of illustration, FIG. 8A shows an ultrasound probe angle 802 of approximately forty-five degrees to the body guide 801, compared to the ninety degree angle between the axis of the medical instrument guide 203 and the body guide 801. Different pre-determined angles between the ultrasound probe 202, the medical instrument guide's 203 propagation axis 204, and body guide 801 can be designed via different geometries of these components in the mount 199.

Knowledge of the position and orientation of the medical instrument guide and therefore propagation axis of the needle relative to the volumetric dataset produced by the probe is determined through a separate calibration process. The position and orientation can be described mathematically in different ways according to those familiar with the art, such as a coordinate system transform describing three Cartesian translations (x, y, z) and three rotations about Cartesian axes (roll, pitch, yaw). Such a transformation describes both the propagation axis of the medical instrument guide and a zero point or reference mark 1201 relative to the volumetric dataset (see FIG. 12). An alternative representation describes the propagation axis of the medical instrument guide as a point (a, b, c) on the propagation axis and a vector (d, e, f) describing the direction of the axis in Cartesian coordinates. The mount may rigidly attach to the probe in a repeatable and accurate manner so that the position and orientation of the medical instrument guide relative to the volumetric dataset is fixed. The volumetric dataset produced by the probe is at a fixed position relative to the probe because of the fixed position of the ultrasound transducers in the probe that emit the beams of ultrasound in the volume. This means that the calibration can be performed once at the time of manufacture of the apparatus 200. Such a pre-determined calibration can be incorporated as a constant parameter into a software module 911 of the system 900 (see FIG. 9).

Figure 8B:
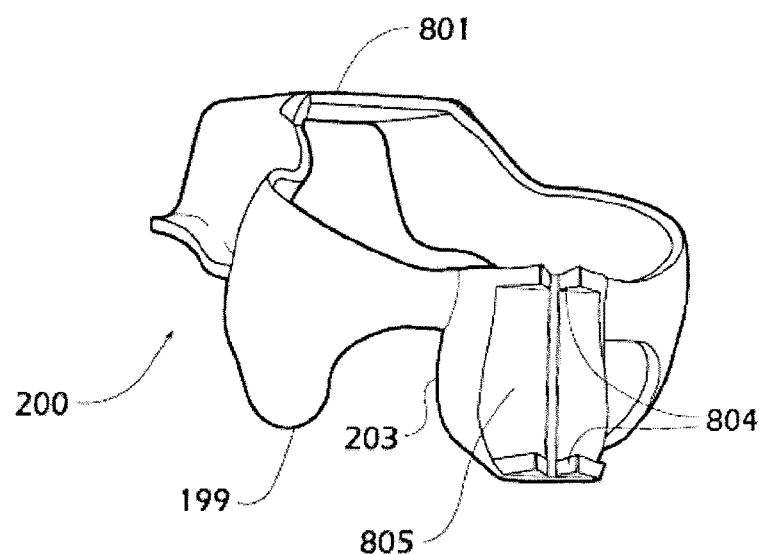
FIGS. 8B and 8C are schematic perspective views of the mount, body guide and medical instrument guide apparatus.

As can also be seen in FIG. 8B, the apparatus 200 contains a finger landing 805 on the medical instrument guide 203. The finger landing 805 is a flat or curved surface surrounding the open channel (groove) of the medical instrument guide 203. As shown in FIG. 3, the operator's finger 301 may engage the exposed portion of the medical instrument (not shown) in the guide 203 by pressing the finger against the finger landing 805 (see FIG. 8B) and holding the medical instrument securely in the channel. Accordingly, removing the medical instrument may be as easy as releasing a finger from the finger landing. In an alternative embodiment (not shown), the thumb may used instead of the finger.

The open channel is defined at a depth that is smaller than the diameter of the medical instrument (for example a needle). The force of the finger on the exposed portion of the needle can control the level of friction of the needle in the medical instrument guide. This control of friction may helps in two ways. First, the operator can apply a very large force to secure the medical instrument in the medical instrument guide when needed (e.g. when attaching a syringe to the needle without accidentally advancing the needle into the body or along the guide). Second, the operator can apply a very small force so the medical instrument moves with little friction in the channel when advancing the medical instrument into the body. With most conventional needle guides, the channel is closed and always provides a significant amount of friction, such that the needle insertion feels "sticky" and is advanced in a start-stop fashion. This uncontrollable amount of friction with most conventional needle guides is unwanted because it makes it difficult for the operator to feel the body's resistance of the needle insertion, such as when the needle encounters stiff tissues, such as ligaments.

Referring to FIG. 8B, the apparatus shows v-notches 804 surrounding the channel of the medical instrument guide 203. The v-notches 804 provide a controlled pathway for a medical instrument to be inserted into the channel of the medical instrument guide 203, which is typically the same width as the medical instrument. This may make it is easier for the operator to place the medical instrument in the channel and to snap the medical instrument back into the channel if the medical instrument is accidentally released from the channel.

Figure 8C:
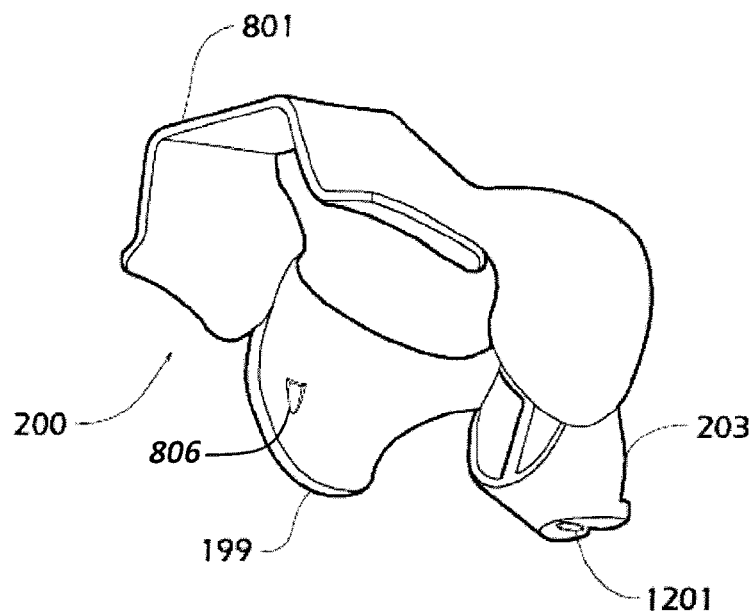

Referring to FIG. 8C, the mount 199 incorporates the medical instrument guide 203 and body guide 801 in a single-piece construction that may be mounted to an ultrasound probe (not shown). The single-piece construction has an appropriate shape and flexibility to be mountable easily and securely on a probe, so that once mounted, it will remain fixed on the probe as long as forces on it remain reasonably small. It can still be removed from the probe by applying large forces. The shape and flexibility also allow the mount 199 to be fit over a thin sterile drape (not shown) covering the ultrasound probe. The tight and secure fit of the mount 199 to the probe ensures the sterile drape will remain tightly covering the probe during scanning of the body. Most conventional needle guides attached directly to the probe with a drape placed over the combination of probe and medical instrument guide and secured with elastic bands. This embodiment of the invention removes the need for elastic bands to hold the drape in place.

Referring to FIG. 8A, the mount 199, medical instrument guide 203 and body guide 801 are at fixed positions relative to each other because of the substantially rigid nature of the mount and guides. When the mount 199 is mounted to the probe 202, the contact between the mount 199 and the probe 202 further constrains the possible flexibility of the mount 199 and thereby further fixes the relative positions of the probe 202, medical instrument guide 203 and body guide 801.

Referring to FIG. 8A, the mount 199 has a geometric shape that substantially matches the geometric shape of a portion of the probe 202. The geometric shape can be chosen to provide a unique match to a particular portion of the probe 202, thereby ensuring that the mount 199 is mounted on the probe 202 at a preferred position. The unique match between the geometry of the mount 199 and probe 202 provides a fixed geometric relationship between the medical instrument guide 203 and the volumetric dataset (not shown). This fixed geometric relationship can be determined by knowledge of the geometry of the relative positions of the volumetric dataset, medical instrument guide 203, probe 202 and mount 199. The mount 199 can also contain one or more alignment markings 806 (see FIG. 8C) that indicate correct alignment between the mount 199 and the probe.

Referring to FIG. 8A, there is a gap between the upper extent of the medical instrument guide 203 and the body 101 that allows the operator to use the free hand to advance the needle 405 into the body 101 by using pinch-grip move-and-release movements on the portion of the needle in the gap.

Referring to FIG. 9, a data processing and imaging system 900 incorporating the apparatus processes and displays the images obtained by the apparatus. In the system 900 shown in FIG. 9, the probe 202 is connected to a transmit/receive (T/R) switch 901. The T/R switch 901 receives signals from a beam transmitter 902 and outputs signals to the probe 202. The T/R switch 901 also transmits signals from probe 202 to a beam receiver 903 that forms echo signals for processing. Both the beam transmitter 902 and the beam receiver 903 are communicative with and controlled by a system controller 907. The beam receiver 903 outputs echo signals (representing 3-D volume datasets) from probe 202 to a signal processor 904, which performs functions such as, but not limited to, digital filtering, contrast detection and enhancement, spectral analysis and B-mode processing; both beam receiver 903 and signal processor 904 are controlled by the system controller 907. Signal processor 904 outputs the modified echo signals to a 3-D image rendering module 905 which converts the 3-D volumetric datasets into 2-D images using a method such as, but not limited to, thick reslicing. The 3-D image rendering is performed according to instructions provided by the system controller 907, which can receive input from a user interface 908 to determine methodology. The 3-D image rendering can use the medical instrument guide-to-volumetric dataset calibration 911 to determine the spatial position of the propagation axis of the medical instrument guide within the volumetric dataset, and thereby select an appropriate rendering such as a 2-D thick slice about a plane that includes the medical instrument. 2-D image data sets are transferred into an image memory 906 for access by the user interface 908, for display on an image display device 909 such as a computer screen, and/or for long-term storage on a storage device 910 such as a hard drive. The image memory 906 communicates with the system controller 907 and the user interface 908 to access datasets and control filing. The user interface 908 can receive commands from a user to control the operation of the system 900, how image data is processed and displayed on the image display device 909, and to access/store images in the long-term image storage device 910. The user interface 908 includes an interface program that may be integrated with the image display device 909 and may include, but is not limited to, a pointing device such as a mouse or touch screen, a keyboard, or other input devices such as a microphone. The system controller 907 communicates with user interface 908 to relay operational and display instructions and operational status. The system controller 907 communicates with the image display device 909 to synchronize the data stream.

Figure 10:
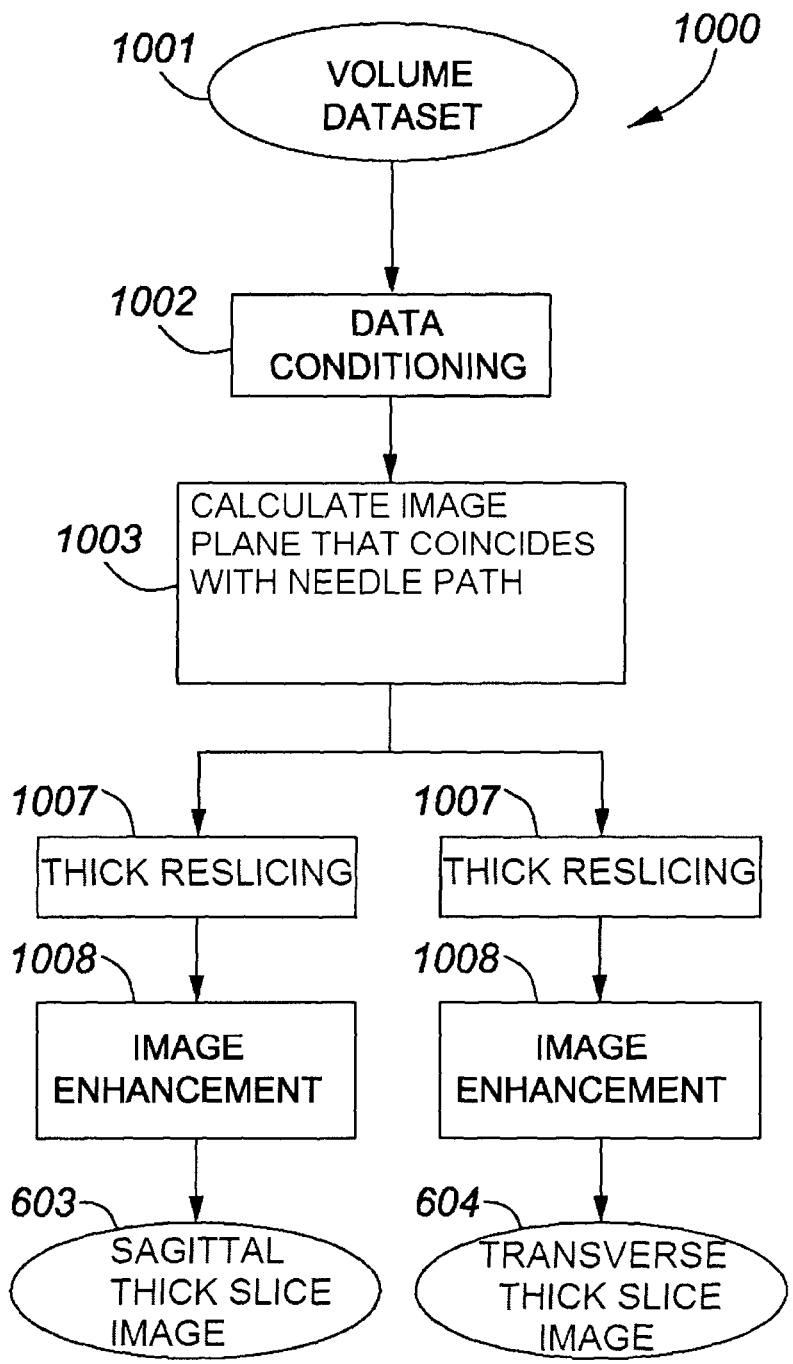
FIG. 10 is a flow chart of a method for processing data from the 3-D volumetric datasets captured by the ultrasound imaging and needle guiding apparatus.

Referring to FIGS. 9 and 10, a data processing method 1000 is carried out by the system 900 to manipulate the 3-D volumetric dataset acquired by the ultrasound probe to produce a 2-D thick slice sagittal plane image 603 and a 2-D thick slice transverse plane image 604 (see FIGURE ii), which can be displayed on the image display device 909. First, the volumetric dataset is obtained from the apparatus (step 1001) and transmitted via T/R switch and beam receiver 903 to the signal processor 904 for data conditioning (step 1002). Data conditioning performed on the 3-D volumetric dataset may include, but is not limited to: filtering, enhancement, thresholding, smoothing and feature extraction. The signal processor 904 also calculates the thick slice portion of the volumetric dataset (step 1003); this step can be performed using the calibration 911 of the medical instrument guide to the volumetric dataset. The thick slice portion is then transmitted to the image rendering device 905 for thick slice cross-sectional (step 1007) image processing.

Instead of a separate signal processor 904, image rendering module 905, controller 907 and memory 906, the steps of the method shown in FIG. 10 can be stored on computer readable medium that can be executed by a general purpose computing device. Examples of suitable computer readable medium are compact disk read only memory (CD-ROM), random access memory (RAM), or a hard drive disk.

When carrying out the thick slice image processing in step 1007, the slab of data used to create the 2-D thick slice image can be taken from the thick slice portion encompassing the sagittal plane, and transverse plane (which are the planes that intersect the medical instrument guide for needle insertion), or on another image plane inputted by the user or automatically selected. The conversion of the slab of data in the thick slice portion into a 2-D thick slice image can be performed by merging the data in the direction perpendicular to the cross-sectional plane of the slab. The merging of the data in the perpendicular direction is performed by weighted averaging after data conditioning. The weighting of the data points is chosen to enhance the depiction of the instrument and target.

The resultant 2-D thick slice image is then processed by the rendering device 905 for image enhancement (step 1008), which may include, but is not limited to, filtering, enhancement, thresholding, smoothing, feature extraction and graphical overlays 1302 (see FIG. 11) and results in the final images. In particular, a graphical overlay 1302 of the anticipated needle trajectory along the propagation axis can be superimposed onto the thick slice images 603 and 604. The location of the overlaid trajectory of the propagation axis is known and fixed relative to the probe, because it is determined by the physical position of the medical instrument guide on the apparatus and is known from calibration 911. Calibration determines the position of the propagation axis of the medical instrument guide relative to the volumetric dataset. The enhanced images are then ready for display by image display device 909, and/or storage on storage device 910. The final images are the thick slice sagittal image 603 and the thick slice transverse image 604.

Figure 11:
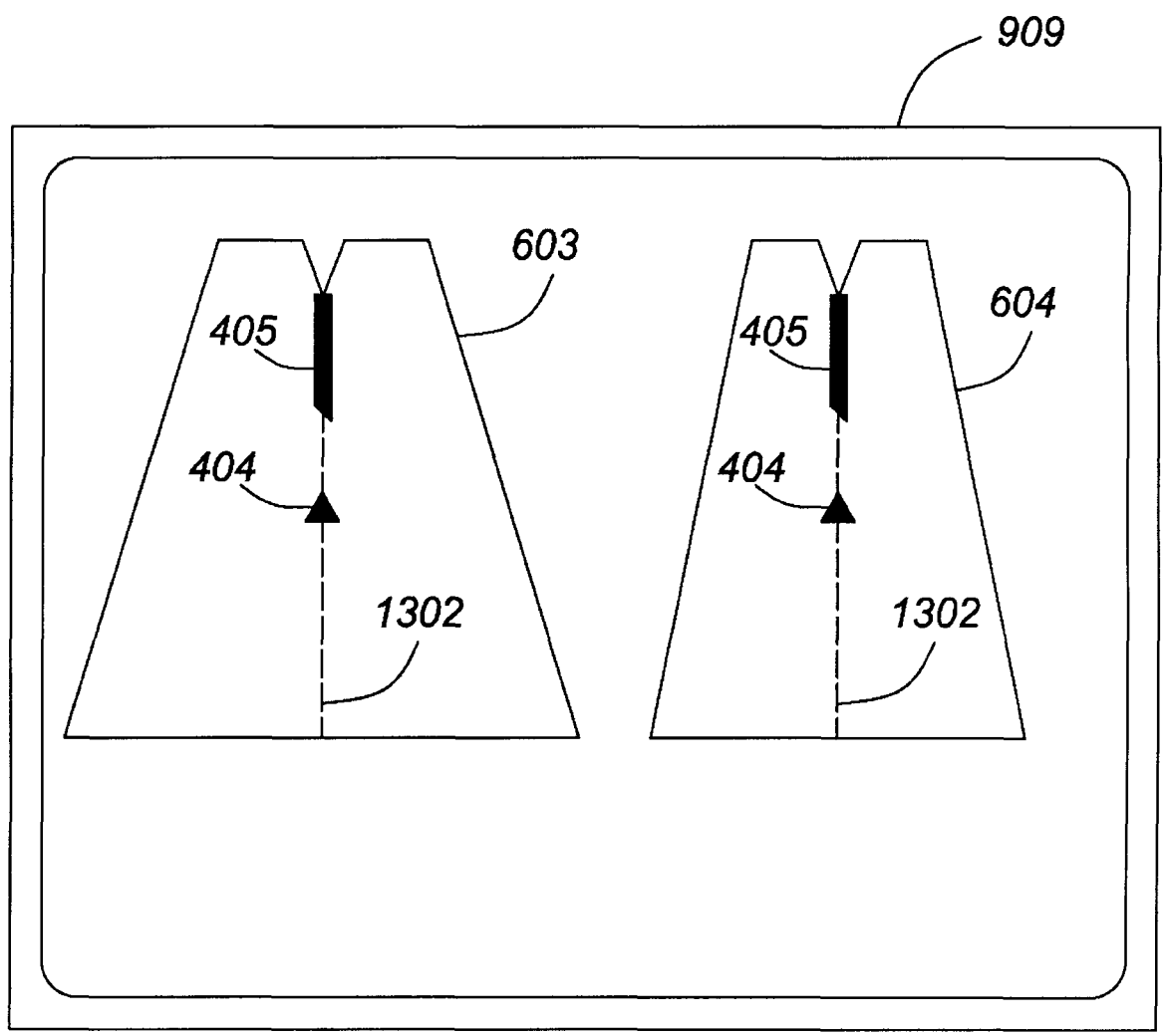
FIG. 11 is a schematic view of a display device displaying multiple images captured by the 3-D ultrasound imaging and needle guiding apparatus.

Referring to FIG. 11, the thick slice sagittal image 603 coincides with a plane that is sagittal to the patient and intersects the graphic overlay 1302 of the propagation axis of the medical instrument guide. This sagittal plane, in which thick slice image 603 is formed, can be the same plane as formed by axes M-M and C-C (see FIGS. 1 and 3). As the operator inserts the medical instrument (needle 405) into the tissue, the needle 405 becomes visible in the image 603, and will be along a graphic overlay 1302 of the expected needle trajectory along the propagation axis. As the needle 405 is inserted deeper into the tissue, more and more of the needle 405 becomes visible in the image 603. The operator aligns the graphic overlay 1302 of the propagation axis with the target 404 so that subsequent insertion of the needle 405 into tissue reaches the target 404. This image 603 is updated on the image display device as the ultrasound 3-D volumetric dataset is created by probe. In this way, the apparatus provides current images of the needle insertion procedure.

Similar steps as described above can be applied to produce the thick slice transverse image 604.

Conventional 2D cross-sectional ultrasound imaging has several limitations that prohibit ultrasound guidance of a needle to the epidural space in the spine. The first limitation is the inability to depict clearly the target epidural space when the probe is placed in the mid-sagittal plane (also known as the median longitudinal plane) where the needle insertion usually takes place. The reason that the epidural space does not appear clearly in this view is because of the presence of the interspinous ligament and spinous processes that fall in the mid-sagittal plane and these structures do not allow the ultrasound beam to penetrate to the epidural space located beneath these structures. It is known that the target epidural space is best imaged by ultrasound in the paramedian plane, where the ultrasound probe is placed on the spinae erector muscle on the left or right of the mid-sagittal plane. A second limitation of conventional 2D ultrasound is that a paramedian placement of the probe means that the imaging plane does not coincide with the plane of needle insertion, so it is impossible to see both the needle in the imaging plane during the entire time it is being inserted. A third limitation is that placing the conventional 2D ultrasound probe in the mid-sagittal plane obscures the puncture site of the needle. The present apparatus combines the paramedian placement of the probe with high-quality depictions of both the epidural space and needle in the same image.

The above-described embodiments provide a solution by using thick-slice imaging from a 3D ultrasound probe. The probe can be placed paramedian to the mid-sagittal plane and a volumetric dataset is acquired over a volume that includes the mid-sagittal plane. The thick slice image in the sagittal plane is created from a slab of data that extends a few millimetres to the sides of the mid-sagittal plane. A slab thickness of a few millimetres is sufficient to include a clear depiction of the target epidural space. During ultrasound scanning, the needle is inserted in the mid-sagittal plane and the highly reflective nature of the needle means it appears clearly in the slab of ultrasound data. By combining together the data in the slab into the thick slice image, both the needle and target can be clearly seen.

Operation

Figure 13:
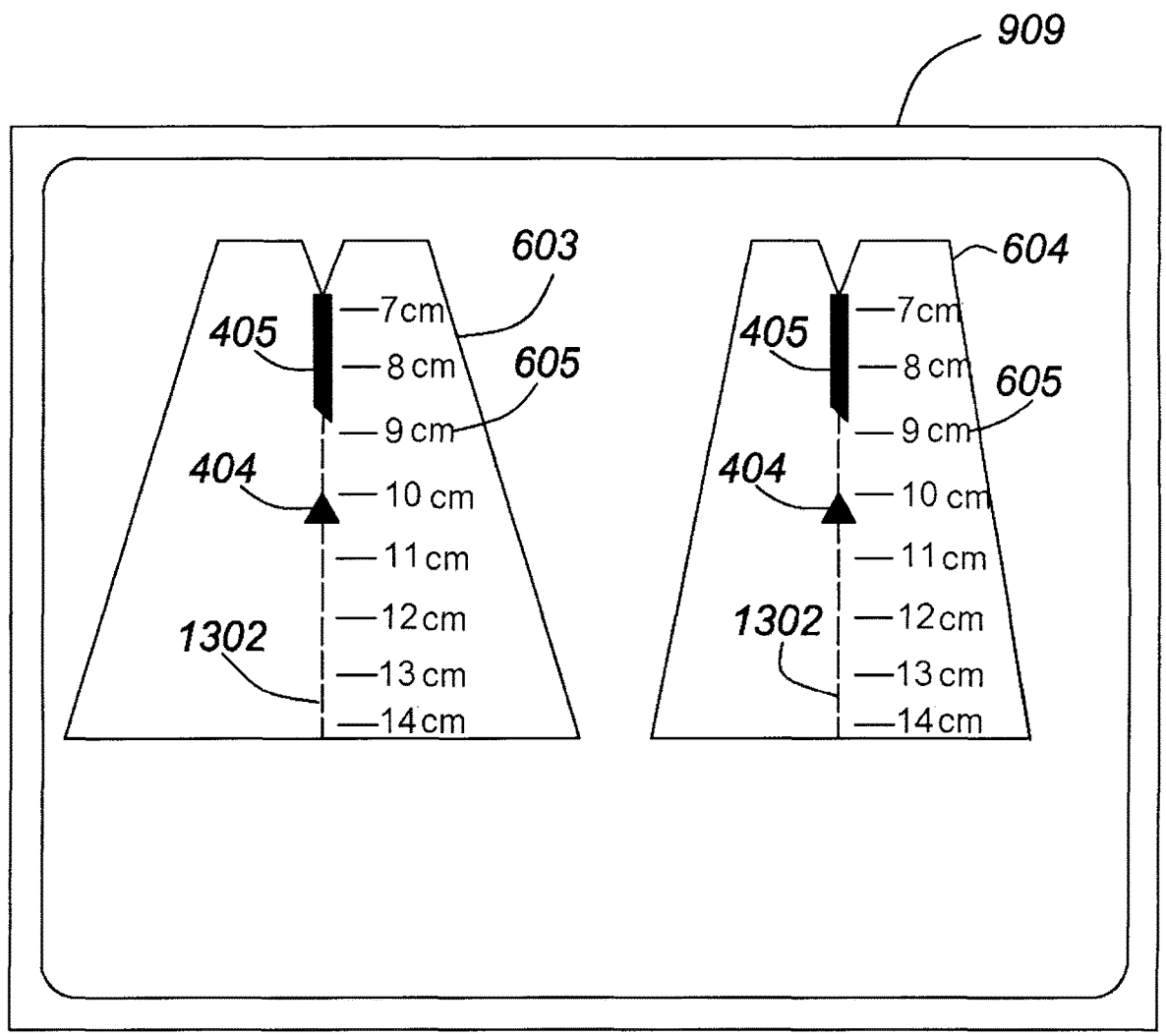
FIG. 13 is a schematic view of a display device displaying multiple images captured by the 3-D ultrasound imaging and needle guiding apparatus, according to another embodiment of the invention, along with centimeter graduations on the overlay of the calculated anticipated trajectory along the propagation axis of the needle.

For example, to illustrate the operation of an embodiments, and referring to FIG. 3, in performing an epidural anaesthesia procedure on a patient using the apparatus 200, an operator holds the apparatus 200 with one hand and places the apparatus 200 against the patient's back so that the medical instrument guide 203 is directly over the needle insertion point iii. The operator adjusts the position of the apparatus 200 until the body guide 801 lies flat against the surface of the body 101, which ensures the propagation axis 204 of the medical instrument guide 203 is substantially perpendicular to the body. The operator then activates the apparatus 200 to cause ultrasound signals to be emitted by the probe 202 and consequent data to be collected and processed by the system 900 and displayed as 2-D images on the image display device 909 (see FIG. 9). The operator aligns the displayed target 404 (e.g. the epidural space) with the superimposed graphic 1302 (see FIG. 11) of the anticipated needle trajectory along the propagation axis 204 in the ultrasound image(s). Because the body guide 801 is pressed flat against the surface of the body 101, the operator is constrained to sliding movements of the apparatus 200 across the body. This constrained motion permits the operator to easily align the target 404 with the superimposed graphic overlay 1302 of the anticipated needle trajectory along the propagation axis 204 while maintaining the propagation axis 204 substantially perpendicular to the body 101. The position of the medical instrument guide 203 on the mount 199 allows the operator to secure the medical instrument (not shown in FIG. 3) in the medical instrument guide with a finger 301 on the same hand that is holding the apparatus 200 (see FIG. 3). The operator then advances the medical instrument into the body 101 with the hand that is not gripping the apparatus 200. The operator may then view in real time on the image display device 909 a processed ultrasound image of the needle tip and needle body and the patient's back and spine (see FIGURE ii), such as the two thick slice images of the sagittal and transverse planes as shown in FIG. 13. The operator may then determine, by viewing the relative motion of the needle tip with respect to the spinal anatomy, when the needle 405 has reached the target (epidural space of the spine). Optionally, the operator then detaches the needle 405 from the medical instrument guide 203 so that the operator can use both hands to perform a loss-of-resistance to saline procedure to ensure the needle 405 has reached the target 404 (epidural space) and insert a catheter or inject an anaesthetic agent.

A similar procedure as the one described above may be carried out to perform a lumbar puncture, where a needle is also inserted through the dura mater into the subarachnoid space.

As can be appreciated from the above discussion, one advantage possible with an embodiment of apparatus is the ability to capture an image of the target, nearby anatomy, and medical instrument trajectory for display in the same display device. Another potential advantage is the ability to acquire more than one image of the target, nearby anatomy and needle trajectory through the use of a 3-D ultrasound probe. Yet another possible advantage is the ability to use the optimal locations on the body surface, also known as "windows", for viewing the spine with ultrasound. Yet another possible advantage is the ability to place the medical instrument through the medical instrument guide near the middle of the apparatus so that the footprint of the apparatus does not interfere with the puncture site of the medical instrument. Yet another potential advantage is the use of thick slice images that depict the medical instrument and target clearly even when the medical instrument path has small deviations from the transverse and sagittal cross-sections of the volume. Yet another possible advantage is the use of a body guide to constrain the medical instrument to a perpendicular insertion through the surface of the body. Yet another possible advantage is the use of an open channel (groove) in a finger-landing on the medical instrument guide, which allows easy releasing of the medical instrument from the medical instrument guide, and allows for operator-controlled friction of the motion of the needle. Yet another potential advantage is the use of v-notches above the open channel (groove) of the medical instrument guide to allow ease of insertion of the medical instrument into the channel. Yet another potential advantage is the single-piece construction that incorporates the mount, medical instrument guide and body guide, and that is easily mountable to the ultrasound probe. Yet another possible advantage is the presence of a gap between the medical instrument guide and the body that allows the operator to use the free hand to advance the medical instrument into the body by using pinch-grip move-and-release movements on the portion of the needle in the gap. Yet another potential advantage is the fixed calibration between the medical instrument guide and the volumetric dataset that provides reliable imaging of the plane containing the medical instrument. Yet another potential advantage is the secure attachment of a sterile drape between the mount and the probe.

Other Alternate Embodiments

According to another embodiment, the operator performs the loss-of-resistance technique or catheter insertion or administration of anaesthetic or analgesic while the medical instrument is still inserted into the medical instrument guide. This embodiment has the potential advantage of reducing the number of steps before catheter insertion or injection of anaesthetic agent in an epidural procedure. In particular, the operator can stop advancing the needle just prior to the needle reaching the target, tightly secure the medical instrument in the channel of the medical instrument guide by pressing a finger firmly onto the finger landing, and attach a fluid-filled syringe (not shown) to the medical instrument (i.e. needle). The operator can then alternate between advancing the needle and pressing the plunger of the syringe to assess the resistance of fluid insertion into the body. The operator may stop advancing the needle when a loss-of-resistance is felt, indicating that the needle tip has reached the target. During the needle insertion procedure, one hand is used to hold the apparatus and the needle in the channel in the medical instrument guide, while the other hand advances the needle and presses the plunger of the syringe. This method has the potential to be a single-person needle insertion procedure.

Figure 15:
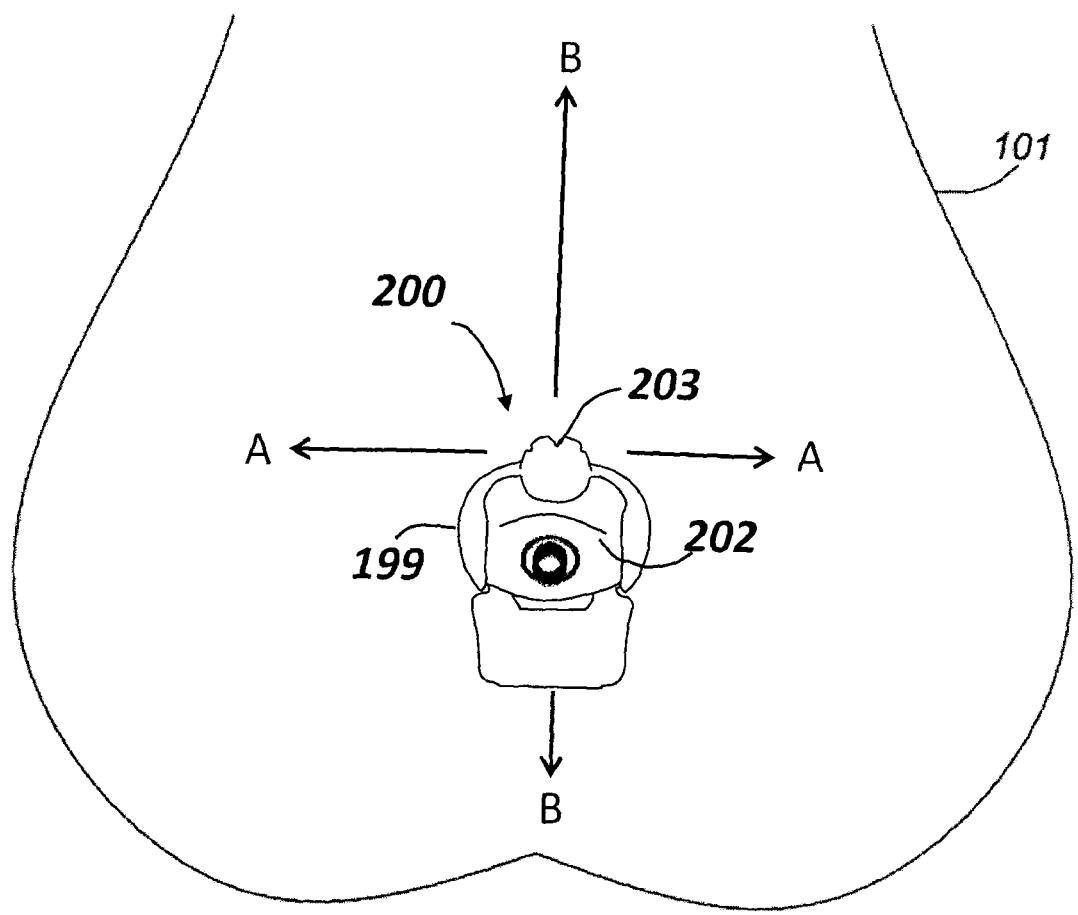
FIG. 15 is a schematic back view of a 3-D ultrasound imaging and needle guiding apparatus according to another embodiment of the invention and positioned to image the spine of the patient from a midline axis of the spine, and rotated ninety degrees from the position indicated in FIG. 2.
Figure 16A:
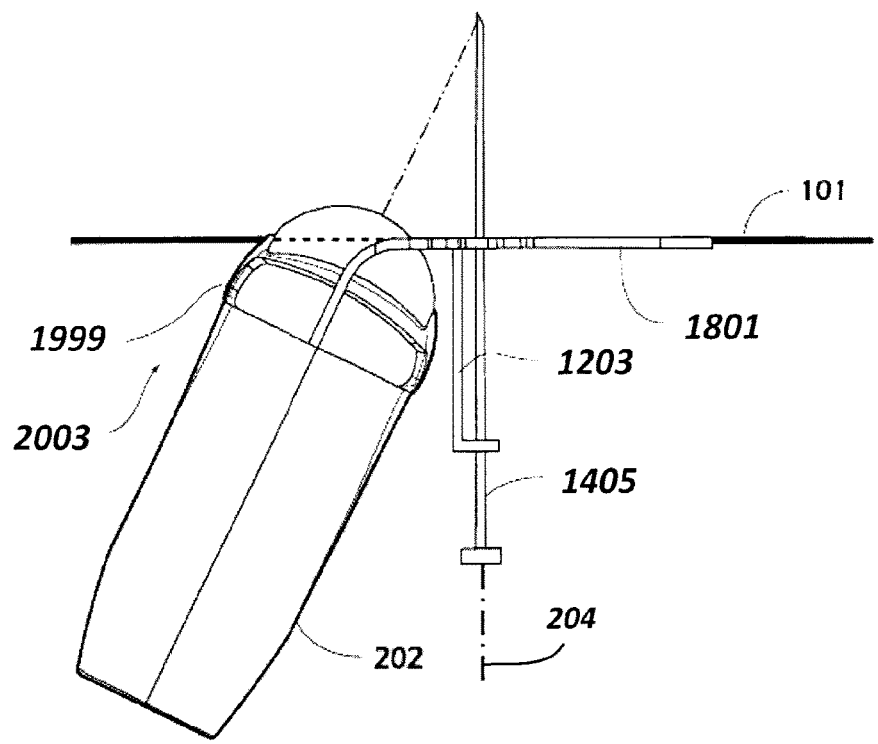
FIG. 16A is a schematic top view and FIG. 16B is a schematic perspective view of a 3-D ultrasound imaging and needle guiding apparatus according to another embodiment of the invention where the body guide is on the opposite side of the needle insertion point than the probe.
Figure 16B:
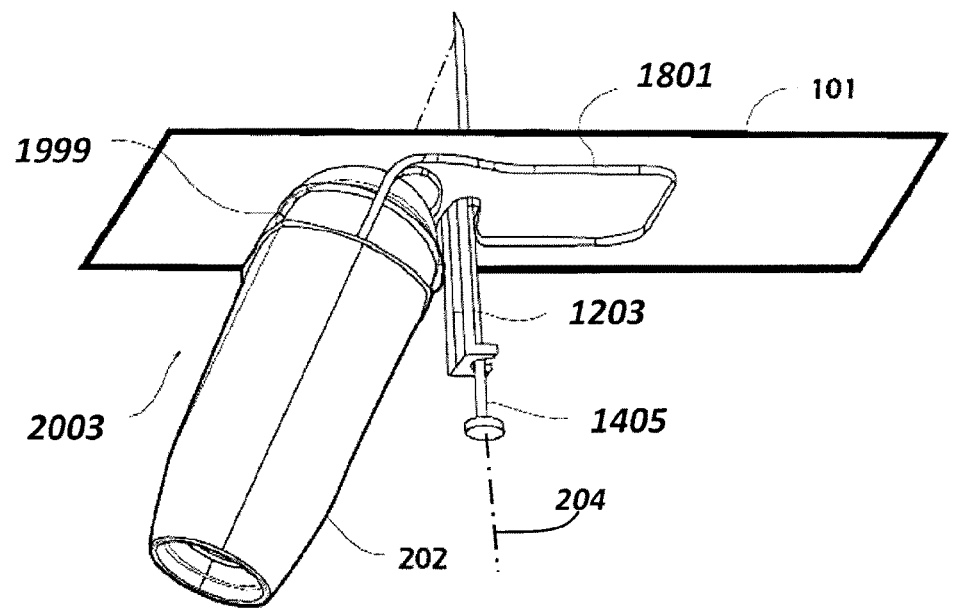

Referring to FIG. 15 and according to another embodiment, the apparatus 200 can be used in an orientation different than that shown in FIG. 2. In the orientation shown in FIG. 15, the axis B-B of the apparatus 200 is aligned approximately to the midline of the spine M-M (see FIG. 1), while the axis A-A is aligned approximately to the left and right of the patient along transverse axis T-T (see FIG. 1). In this orientation, the propagation axis of the medical instrument guide 203 is aligned with the axis C-C, which is the horizontal axis extending through the needle insertion point iii (see FIG. 3) and is directed towards the patient's back in the anterior-posterior direction. A thick slice of the volumetric dataset in the plane containing the axes A-A and C-C covers anatomy from both the left and right side of the spine, so the symmetry of the spine's appearance in the image can be used for adjusting the position of the apparatus 200 such that the propagation axis of the medical instrument guide intersects the midline axis of the spine M-M. This embodiment has the advantage that the operator may mark the body surface at the centerline of the spine to create a visual aid for faster positioning of the apparatus as shown in FIG. 2 for subsequent needle insertion.

Referring to FIG. 16 and according to another embodiment, the medical instrument guide 1203 is between the probe 202 and the body guide 1801 and is still attached to the mount 1999. For comparison, FIGS. 5, 6 and 8 show the body guide 801 and the probe 202 on the same side of the medical instrument guide 203. This embodiment has the potential advantage of allowing the palm of the operator's free hand to press the body guide 1801 firmly against the body 101 while advancing the needle 1405 into the body with the fingers.

Referring to FIG. 3 and according to another embodiment, the apparatus 200 can be used in an orientation flipped to the right side of the body (not shown). This embodiment is simply the mirror version of the placement of apparatus shown in FIG. 3, where the probe is instead placed on the right side of the body. This embodiment has the potential advantage of allowing an operator to use the right hand to hold the apparatus 200, and the left hand to insert the needle for operators who are left-handed. In FIG. 3, the apparatus 200 is held in the left hand and the right hand is used to insert the needle.

Referring to FIG. 6 and according to another embodiment, the probe 2202 may be linear or phased array probe. In this embodiment, the size and shape of the 3-D volumetric dataset 402 are determined by the flat shape of the probe 2202 and the beam steering directions. This embodiment has the possible advantage of using linear or phased array probes that can offer improved image quality through a trade-off with field-of-view.

In yet another embodiment (not shown), the probe, whether flat or curved, can be further angled toward the medical instrument guide so that the beams intersect the medical instrument at angles even closer to perpendicular and a stronger echo from the medical instrument is obtained. This has the possible advantage of providing a better depiction of the medical instrument in the images produced by a system described herein.

Referring to FIG. 7 and according to another embodiment, the probe 202 images the smallest volumetric dataset 402 that encloses the thick slice 403. This embodiment has the possible advantage of acquiring a smaller volumetric dataset at a faster rate than a larger volumetric dataset, which allows faster processing by the data processing and imaging system.

Figure 12:
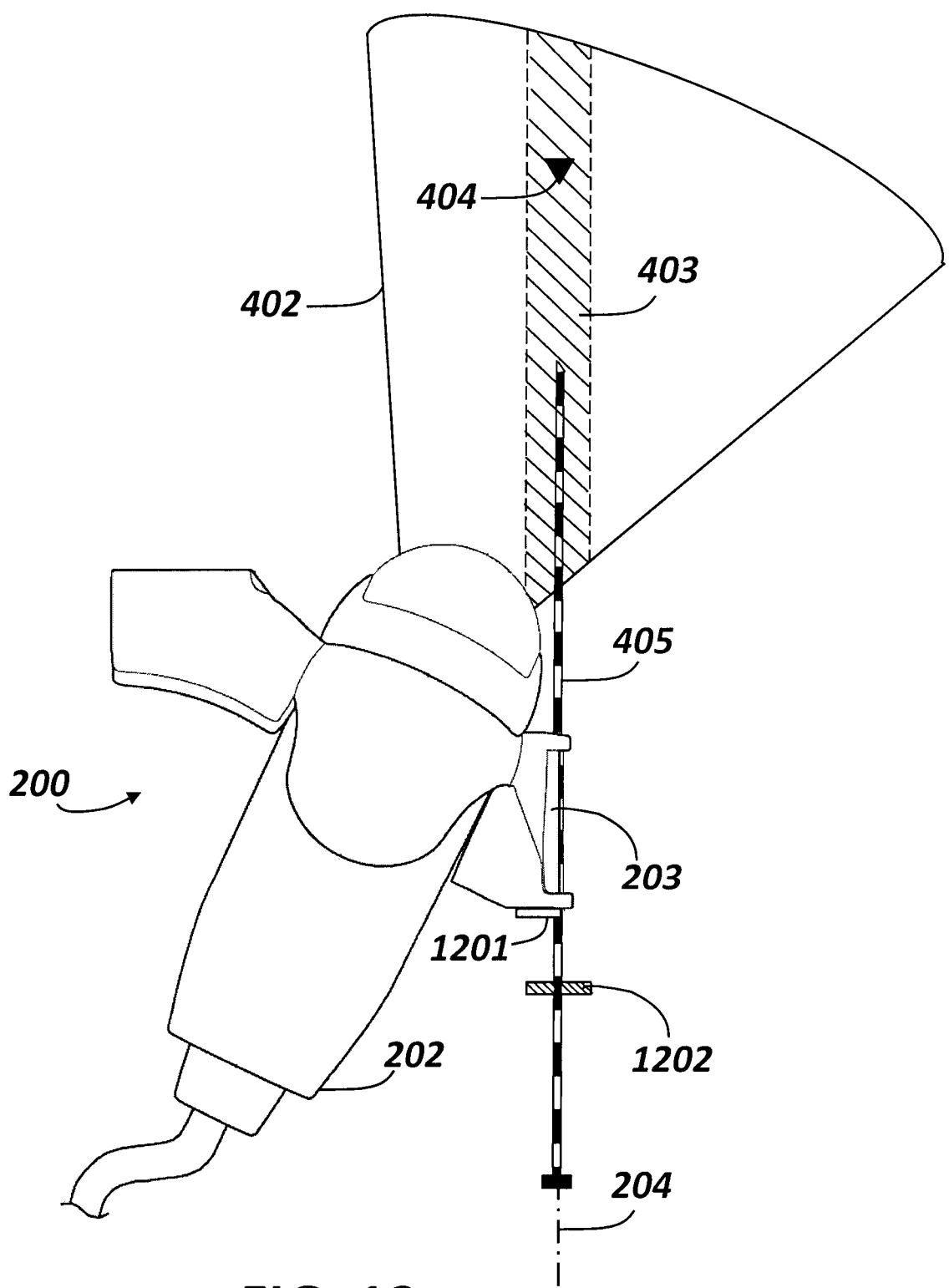
FIG. 12 is a schematic top view of the ultrasound probe of the 3-D ultrasound imaging and needle guiding apparatus, according to another embodiment of the invention, along with a representation of the spatial extent of the volumetric dataset captured by the ultrasound probe, and an indicator mark for the origin of the depth measurements of the needle insertion.

Referring to FIGS. 8C and 12, and according to another embodiment, the medical instrument guide contains a reference mark 1201 or other indication for the origin of the measurement of the needle insertion depth. The reference mark can be the number zero, or any other indication of an origin. The location of the reference mark 1201 relative to the 3D volumetric dataset 402 is known through calibration and remains fixed during operation of the system. This embodiment has the advantage of using the fact that most epidural needles have a series of black etchings spaced 1 cm apart (see FIG. 12) to allow the operator to count the centimeters of needle insertion relative to graduations shown on the 2-D ultrasound image. The graduations 605 are shown in FIG. 13 as graphical overlays superimposed on the thick re-slice images 603 and 604. With this embodiment the operator may align the displayed target 404 (for example, the epidural space) with the superimposed graphic 1302 of the anticipated needle trajectory along the propagation axis 204 in the ultrasound image(s) and observes the depth of the target 404 relative to the graduations 605. In FIG. 12, the target is at 10 cm depth, as an example. The needle 405 is subsequently inserted through the medical instrument guide 203 while the depth of insertion is observed by counting the centimeter etchings on the needle relative to the mark 1201. The operator stops insertion of the needle 405 at a depth less than or equal to the depth of the target 403, as determined by counting. This embodiment has the advantage that the needle 405 does not need to be clearly visible in the image display device 909, only the target 403 needs to be visible, and that overshoot of the needle 405 past the target 403 can be avoided by observing the depth of the insertion of the needle 405.

According to yet another embodiment, a component of the medical instrument guide, such as a grommet 1202 (see FIG. 12), which may be rubber, is attached by the operator to the needle 405 at the depth of the target 403 as indicated by the graduations 605 that are related to the origin at the mark 1201. The grommet is attached before needle insertion and serves as a visual aid to ensure that the needle 405 insertion does not overshoot the target 404. As an example, in FIG. 12 and FIG. 13, the target depth is 10 cm and the needle is shown inserted to a depth of 9 cm, so the grommet is 1 cm away from the mark. This embodiment has the potential advantage that the operator does not need to count the black etchings relative to the mark 1201, but only needs to stop insertion of the needle 405 when the grommet 1202 reaches the mark 1201.

According to yet another embodiment (not shown), the medical instrument guide is not permanently or detachably mounted to the mount and instead is a component of the apparatus that is located remotely of the probe and mount. Both the apparatus and needle are provided with a position tracking system that provides measurements of the needle position and orientation relative to the ultrasound probes. The tracking system can be based on electromagnetic tracking of coils placed on both the medical instrument and the apparatus. A tracking system can also be based on optical tracking of both the medical instrument and the apparatus. Furthermore, a tracking system can be based on a moveable medical instrument guide connected to the apparatus by one or more linkages with angle sensors on the linkage joints. With any such needle position tracking system, the expected needle trajectory can be calculated from the measured needle position and orientation instead of using a fixed calibration. This expected needle trajectory can be shown as a graphic overlay on any of the images. In use, the operator can position the medical instrument guide such that the propagation axis of the projected trajectory falls within the volumetric dataset of the probe and thus is displayable on the image display device.

According to yet another embodiment (not shown), the medical instrument guide is permanently or detachably mounted to the mount, and is used together with a position tracking system to provide measurements of both the apparatus and needle relative to the probe. The medical instrument guide determines the fixed propagation axis of the needle and the position tracking system determines the location of the needle along the propagation axis. This embodiment has the potential advantage of constraining the needle to a fixed propagation axis with respect to the apparatus, which improves ease-of-use, combined with measurements of the location of the depth of needle insertion from the position tracker. By using both a medical instrument guide and position tracking, the location of the needle tip can be shown graphically on the image display device using the position tracker measurements, while retaining the graphic overlay of the fixed trajectory and graduations. This also has the potential advantage of not requiring clear visibility of the needle in the images.

According to yet another embodiment, the apparatus 200 is first positioned left of the sacrum 108 (see FIG. 1) so that the display of the sagittal thick slice 603 (see FIG. 11) image shows the sacrum 108. The apparatus is then moved up by the operator along axis P-P so that it slides along the side of the spine until it reaches the position 110. The possible advantage of this operation of the device is that the operator can count the vertebrae as the apparatus slides from the sacrum 108, then past L5 107 and L4 106 until it reaches the position 110. By counting the number of vertebrae displayed on the image display device 909 as the apparatus 200 moves past the vertebrae, the operator can select the desired intervertebral space for the needle insertion, which is normally between L3 105 and L4 106 for epidurals or lumbar punctures, as shown in FIG. 1. A different desired intervertebral space can be chosen by counting a different number of vertebrae from the sacrum 108 as the apparatus 200 is moved along axis P-P.

In yet another embodiment, the apparatus is first positioned left of T12 102 and moved along axis P-P down the spine until it reached position no. The vertebra T12 102 is the lowest vertebra that contains a rib, so it can be recognized uniquely in the thick slice images. Similar to counting vertebrae up from the sacrum until the apparatus reaches the desired vertebral interspace, this embodiment counts down from T12. A different desired intervertebral space can be chosen by counting a different number of vertebrae from T12 102 as the apparatus is moved along axis P-P.

Referring to FIGS. 17A-D, a further embodiment is shown having a two part apparatus being attached to a probe. In this embodiment, the main components of the apparatus include a 3-D ultrasound probe 202, an upper mount 299, a lower mount 399, a body guide 2801, and a medical instrument guide 2203. In this embodiment, the body guide 2801 and the medical instrument guide 2203 are affixed to the upper mount 199. The upper mount 299 and lower mount 399 are fastened together over the probe 202. The advantage of separate upper mount 299 and lower mount 399, compared to the single piece construction shown in FIGS. 2, 3, 5, 6, 7, 8A, 8B, 8C, 12, 14A, 14B, 15, 16A, 16B, may be that the separate mounts have the potential to eliminate the need for a single mount to substantially flex when mounting securely on the probe. The elimination of flex allows the upper mount 299 and lower mount 399 to be constructed of a substantially rigid material such as stainless steel. In this embodiment, the operator (not shown) places and holds the upper mount 299 on the face of the probe 202 (FIGS. 17A and 17B) and then fastens the lower mount 399 to the upper mount 299 by pressing them together (FIGS. 17B and 17C) until the fasteners are secure. The upper mount 299 and lower mount 399 are shown in FIG. 17 to fasten securely to each other with releasable hook fasteners, but other fasteners may also be used (not shown).

It will be appreciated by a person of skill in the art that the potential/possible advantages discussed above may be available depending on the embodiment and the circumstances under which, an individual embodiment may be used by the operator.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

Other aspects and features of the present invention will become apparent to those ordinarily skilled in the art upon review of the following description of illustrative embodiments in conjunction with the accompanying FIGURES.

While specific embodiments have been described and illustrated, such embodiments should be considered illustrative only and not as limiting the invention.

What is claimed is:
1. An apparatus, the apparatus comprising:
a mount operable to receive a single ultrasound probe;
a body guide positioned relative to the mount such that the single ultrasound probe is constrained to be in contact with a body at an ultrasound probe angle of between 5 degrees and 85 degrees and from which a propagation axis extends toward a target in a body and intersects the target; and
a medical instrument guide operable to receive and guide a medical instrument substantially perpendicular relative to the plane of the body guide, wherein, the mount, the body guide, and the medical instrument guide are monolithically formed; and
wherein the single ultrasound probe, positioned within the mount, is operable to acquire a volumetric dataset representing a 3-D depiction of a volume such that the volumetric dataset comprises information about the medical instrument's position relative to the target in three dimensions.
2. The apparatus of claim 1, wherein the apparatus further comprises the ultrasound probe.
3. The apparatus of claim 2, wherein the ultrasound probe is configured to acquire a volumetric dataset representing a 3-D depiction of a volume.
4. The apparatus of claim 2, wherein the probe is a mechanical 3-D probe or a multidimensional probe.
5. The apparatus of claim 2, wherein the probe is curved.
6. The apparatus of claim 2, wherein the probe is angled towards the propagation axis.
7. The apparatus of claim 1, wherein the ultrasound probe angle, is between 10 degrees and 80 degrees.
8. The apparatus of claim 1, wherein the medical instrument guide is an open channel, having a finger pad on either side of the channel.
9. The apparatus of claim 1, wherein the medical instrument guide is detachably mountable to the mount in one or more orientations.
10. The apparatus of claim 1, wherein the medical instrument guide has a reference mark to assist in determining the depth of the medical instrument insertion along the propagation axis.
11. The apparatus of claim 1, wherein the medical instrument guide comprises means for tracking the position of the instrument relative to the probe.
12. The apparatus of claim 2, wherein the ultrasound probe is configured to acquire the volumetric dataset continuously so that the volumetric dataset comprises real-time or semi-real-time information about the position of the medical instrument relative to the target in three dimensions.
13. The apparatus of claim 2, wherein the ultrasound probe is configured to acquire the volumetric dataset for the smallest volume that encloses the medical instrument and the target.
14. The apparatus of claim 1, wherein the mount comprises markings representing the inferior-superior and left-right axes of the body thereby indicating the desired position of the apparatus on the body.
15. An apparatus, the apparatus comprising:
a body guide having a planar surface operable to position the apparatus adjacent a body substantially parallel relative to the plane of the body, such that a single ultrasound probe is constrained to be in contact with the body at an ultrasound probe angle of between 5 degrees and 85 degrees;

a medical instrument guide operable to receive and guide a medical instrument substantially perpendicular relative to the plane of the body guide; and a mount positioned adjacent the body guide and the medical instrument guide, wherein the mount is operable to receive the single ultrasound probe;

wherein the single ultrasound probe, positioned within the mount, is operable to acquire a volumetric dataset representing a 3-D depiction of a volume such that the volumetric dataset comprises information about the medical instrument's position relative to the target in three dimensions within the body.

16. The apparatus of claim 15, wherein the mount is operable to hold the ultrasound probe in contact with the body at an ultrasound probe angle whereby a propagation axis extends toward the target in the body.

17. The apparatus of claim 15, wherein the apparatus further comprises the ultrasound probe.

18. A system for acquiring and displaying ultrasound medical images, comprising:
(a) an ultrasound imaging and instrument guiding apparatus which comprises:
a single hand-held ultrasound probe, configured to acquire a volumetric dataset representing a 3-D depiction of a volume;
a mount to which the single hand-held ultrasound probe is mounted;
a medical instrument guide positioned relative to the single hand-held ultrasound probe and configured to receive and guide a medical instrument along a propagation axis to a target in a body such that the target and the propagation axis intersect in the volume; and
a body guide having a planar surface operable to position the apparatus adjacent the body substantially parallel relative to the plane of the body, whereby the single hand-held ultrasound probe is constrained to be in contact with the body at an ultrasound probe angle of between 5 degrees and 85 degrees and at an orientation from which the propagation axis can be referenced;
(b) circuitry communicative with the ultrasound imaging and instrument guiding apparatus to receive the volumetric dataset therefrom and comprising a processor with a memory having programmed thereon steps and instructions for execution by the processor to:
condition the volumetric datasets;
calculate an image plane that coincides with the propagation axis;
create a thick-slice image, wherein the thick-slice image represents data from a slab of non zero thickness of the volume encompassing the calculated image plane; and
(c) a display device communicative with the circuitry to receive and display one or more of the thick-slice images.

19. The system of claim 18, wherein the memory is further programmed to enhance the thick-slice image.

20. The system of claim 18, wherein the memory is further programmed to superimpose a graphical overlay representing the propagation axis of the instrument on the image.

21. The system of claim 18, wherein the medical instrument guide has a reference mark to assist in determining the depth of the medical instrument insertion along the propagation axis, wherein the memory is further programmed to superimpose a graphical overlay representing an anticipated trajectory along the propagation axis of the medical instrument including graduations indicating the depth of the medical instrument insertion with respect to the reference mark on the medical instrument guide.

22. The system of claim 18, further comprising a storage device to record the thick-slice image.

23. The system of claim 18, wherein the thick slice of the volume is oriented in the sagittal plane of the body.

24. The system of claim 18, wherein the thick slice of the volume is oriented in the transverse plane of the body.

25. The system of claim 18, wherein the image is created from the thick slice of the volume by a process of merging data in a direction perpendicular to the cross-sectional plane of the thick slice.

26. The system of claim 18, wherein the size of the volume acquired by the probe is determined so that it minimally encompasses the maximum extents of the thick slice used to create the image.

27. The system of claim 21, wherein the reference mark of the medical instrument guide is referenced to show the depth of the thick slice of the volume along the propagation axis.

* * * * *